(12) United States Patent
Muotri et al.

(10) Patent No.: US 9,725,695 B2
(45) Date of Patent: Aug. 8, 2017

(54) STEM CELL DEFINED MEDIA FOR XENO-FREE AND FEEDER FREE CONDITIONS AND USES THEREOF

(75) Inventors: Alysson Muotri, La Jolla, CA (US); Paulo Andre Nobrega Marinho, La Jolla, CA (US); Stevens Kastrup Rehen, Rio de Janeiro (BR); Leda Dos Reis Castilho, Rio de Janeiro (BR)

(73) Assignees: The Regents of the University of California, Oakland, CA (US); Universidade Federal Do Rio De Janeiro, Rio de Janeiro (BR)

( * ) Notice: Subject to any disclaimer, the term of this patent is extended or adjusted under 35 U.S.C. 154(b) by 282 days.

(21) Appl. No.: 13/696,286

(22) PCT Filed: May 5, 2011

(86) PCT No.: PCT/US2011/035427
§ 371 (c)(1),
(2), (4) Date: Nov. 5, 2012

(87) PCT Pub. No.: WO2011/140397
PCT Pub. Date: Nov. 10, 2011

(65) Prior Publication Data
US 2013/0059377 A1 Mar. 7, 2013

Related U.S. Application Data

(60) Provisional application No. 61/331,553, filed on May 5, 2010.

(51) Int. Cl.
*C12N 5/07* (2010.01)
*C12N 5/0735* (2010.01)

(52) U.S. Cl.
CPC ........ *C12N 5/0606* (2013.01); *C12N 2500/25* (2013.01); *C12N 2500/30* (2013.01); *C12N 2500/38* (2013.01); *C12N 2500/98* (2013.01); *C12N 2501/105* (2013.01); *C12N 2501/115* (2013.01); *C12N 2501/15* (2013.01); *C12N 2501/845* (2013.01); *C12N 2501/998* (2013.01)

(58) Field of Classification Search
CPC .......................... C12N 5/0606; C12N 2500/25
USPC .................................................. 435/366, 377
See application file for complete search history.

(56) References Cited

U.S. PATENT DOCUMENTS

| | | | | |
|---|---|---|---|---|
| 5,766,948 A | * | 6/1998 | Gage ...................... | C12M 23/20 435/325 |
| 2005/0032122 A1 | * | 2/2005 | Hwang et al. ................. | 435/7.1 |
| 2010/0068805 A1 | * | 3/2010 | Totey et al. .................... | 435/366 |

OTHER PUBLICATIONS

Ludwig et al., Nature Biotechnology, vol. 24, No. 2, p. 185-187, 2006.*
Rajala et al., Human Reproduction, vol. 22, No. 5, p. 1231-1238, 2007.*
Bendall et al. (Nature, vol. 448, p. 1015-1021, 2007).*
Caamano et al. (Physiology and Management, vol. 81, p. 369-374, 1998).*
Bertheussen et al. (Cytotechnology, vol. 11, p. 219-231, 1993).*
Ludwig et al. (Nature Biotechnology, vol. 24, No. 2, p. 185-187 and supplementary data, 2006).*
ThermoFisher Scientific "11905—Chemically Defined Lipid Concentrate" ThermoFisher Cat. No. 11905031, 1 page.*
Bertheussen, Kjell, "Growth of cells in a new defined protein-free medium," *Cytotechnology*, 1993, 11:219-31 (Exhibit 1).
Chin, Angela Chui Ping et al., "Identification of proteins from feeder conditioned medium tht support human embryonic stem cells," *Journal of Biotechnology*, 2007, 130:320-8 (Exhibit 2).
Fernandes, A. M. et al., "Worldwide Survey of Published Procedures to Culture Human Embryonic Stem Cells," *Cell Transplantation*, 2010, 19:509-23 (Exhibit 3).
Garcia-Gonzalo, Francesc R. and Juan Carlos Izpisúa Belmonte, "Albumin-Associated Lipids Regulate Human Embryonic Stem Cell Self-Renewal," *PLoS ONE*, 2008, 1:e1384 (Exhibit 4).
Levenstein, Mark E. et al., "Basic Fibroblast Growth Factor Support of Human Embryonic Stem Cell Self-Renewal," *Stem Cells*, 2006, 24:568-74 (Exhibit 5).
Lim, Justin Wee Eng and Andrea Bodnar, "Proteome analysis of conditioned medium from mouse embryonic fibroblast feeder layers which support the growth of human embryonic stem cells," *Proteomics*, 2002, 2:1187-203 (Exhibit 6).
Pouton, Colin W. and John M. Haynes, "Embryonic stem cells as a source of models for drug discovery," *Nature Reviews*, 2007, 6:605-16 (Exhibit 7).
Prowse, Andrew B. J. et al., "A proteome analysis of conditioned media from human neonatal fibroblast used in the maintenance of human embryonic stem cells," *Proteomics*, 2005, 5:978-89 (Exhibit 8).
Thomson, James A. et al., "Embryonic Stem Cell Lines Derived from Human Blastocysts," *Science*, 1998, 282:1145-7 (Exhibit 9).
Unger, Christian et al., "Good manufacturing practice and clinical-grade human embryonic stem cell lines," *Human Molecular Genetics*, 2008, 17:R48-53 (Exhibit 10).
Wang, Lisheng et al., "Human embryonic stem cells maintained in the absence of mouse embryonic fibroblasts or conditioned media are capable of hematopoietic development," *Blood*, 2005, 105:4598-603 (Exhibit 11).

* cited by examiner

*Primary Examiner* — Chris R Tate
*Assistant Examiner* — Aaron J Kosar
(74) *Attorney, Agent, or Firm* — Gavrilovich, Dodd & Lindsey LLP

(57) ABSTRACT

The invention provides a defined low protein culture medium for maintaining cells in an undifferentiated state, the medium comprising: a basal medium, an organic acid from the tricarboxylic acid cycle, nonessential amino acids, a combination of growth factors selected from the group consisting of FGF-2 protein, an IGF-1 protein or insulin, a Transferrin protein, and a TGF beta 1 protein, wherein the medium is essentially feeder-free, essentially xeno-free, essentially free of beta-mercaptoethanol, and essentially free of animal-derived or human-derived proteins.

9 Claims, 16 Drawing Sheets

STEM CELL DEFINED MEDIA FOR XENO-FREE AND FEEDER FREE CONDITIONS AND USES THEREOF

This application is a 371 application of PCT application No. PCT/US2011/035427, filed May 5, 2011, which claims priority of U.S. Ser. No. 61/331,553, filed May 5, 2010, the contents of all of which are hereby incorporated by reference in their entirety into the present application.

Throughout this application various publications are referenced. The disclosures of these publications in their entireties are hereby incorporated by reference into this application in order to more fully describe the state of the art to which this invention pertains.

BACKGROUND OF THE INVENTION

Since the first derivation of stem cells (e.g. human embryonic stem cells (hES)) (THOMSON, 1998) much attention has been drawn to the stein cell field, mainly, because of their potential role in cell therapy and regenerative medicine (MOUNTFORD, 2008), as well as their use for screening new targets in drug discovery (POUTON, 2007). However, their use in clinical therapies is limited because an environment free of animal contaminants is necessary due to the highly potential risks involving carrying non-human pathogens in humans (MARTIN, 2005). Additionally, for cultivating stem cells, an environment free of human compounds is imperative since human-preferred pathogens can be carried in this scenario.

hES have been isolated in co-culture with inactivated murine embryonic fibroblasts (MEFs) (THOMSON, 1998), where these cells are working as feeders of the process, releasing factors and matrix that supports hES growth in undifferentiated state (CHIN, 2007). The use of feeder cells provides a huge font of animal contamination but also provides the major sources of variability, since many parameters such as: background and source of mice, confluence and time after plating have been already demonstrated to affect hES culture. It is estimated that over 90% of the research involving hES use feeder co-cultures to maintain pluripotency (FERNANDES, 2010). The main problem in removing co-culturing techniques in stem cell cultures is the lack of knowledge and understanding regarding the key factors released by these cells (LIM & BODNAR, 2002; PROWSE, 2005).

Likewise, the standard media used with feeder cells includes serum-substitutes, e.g., Knockout Serum Replacement (KSR) (Invitrogen), which is replete with animal compounds, thus, making the translation to cell therapy even more difficult. Moreover, its formulation is not fully known (GARCIA-GONZALO, 2008). Once again, this media is used in over 90% of stein cell research (FERNANDES, 2010).

Alternatives to feeder conditioned and KSR based media are main concerns in the stein cell and induced pluripotent stein (iPS) cell fields. Few groups have been able to identify factors and generate new media that do not require feeder cells or even KSR in its formulation (LUDWIG, 2006; WANG, 2007). However, these studies share few things in common; all of them require a non-animal matrix, called Matrigel, as a proper surface for hES attachment. Thus, all media are mainly made of animal components, adding no benefits to the replacement of the KSR. Nevertheless, all of them lack a consistent and robust methodology of optimization, characterized by a lack of an empiric approach, leading to formulations that are not ideal, making animal components replacement for recombinant proteins unfeasible.

In that sense, it is clear that the development of an optimized, chemically defined, xeno-free and cost-effective culture medium must be generated in order to overcome one of the most important bottlenecks for future FDA-approved stem cell therapy.

SUMMARY OF THE INVENTION

The present invention provides a defined low protein culture medium for maintaining stem cells in an undifferentiated state. In one embodiment, the medium comprises: a basal medium, an organic acid from the tricarboxylic acid cycle, nonessential amino acids, a combination of growth factors selected from the group consisting of FGF-2 protein, an IGF-1 protein or insulin, a Transferrin protein, and a TGF beta I protein, wherein the medium is essentially feeder-free, essentially xeno-free, essentially free of beta-mercaptoethanol, and essentially free of animal-derived or human-derived proteins.

The invention also provides a defined low protein culture medium for maintaining stem cells in an undifferentiated state, wherein the medium comprises: Basal medium, a citric acid, Nonessential amino acids, glutamine, Chemically Defined Lipid concentrate (CDL), FGF-2, IGF-1 or insulin, Transferrin, TGF beta 1, Pipecolic acid, γ-aminobutyric acid (GABA), Albumin, and a combination of hepes and sodium bicarbonate, wherein the medium is feeder-free, xeno-free, free of beta-mercaptoethanol, and free of animal-derived or human-derived proteins.

The invention further provides a serum substitute comprising Citric Acid, Sodium Selenite, Nonessential amino acids, Glutamine, bFGF, recombinant albumin, recombinant transferrin and recombinant IGF-1.

The invention also provides methods for maintaining and expanding stem cells in an undifferentiated state in culture comprising culturing the stem cells in a defined low protein culture medium of the invention, which is feeder-free, xeno-free, free of any denaturing agents, and free of animal-derived or human-derived proteins, so as to maintain and expand the stem cells in the undifferentiated state in culture. The medium comprises an organic acid from the tricarboxylic acid cycle and a combination of growth factors selected from the group consisting of FGF-2 recombinant protein, an IGF-1 recombinant protein or recombinant insulin, a Transferrin recombinant protein, and a TGF beta 1 recombinant protein.

DETAILED DESCRIPTION OF THE INVENTION

Definitions

Figure 1:
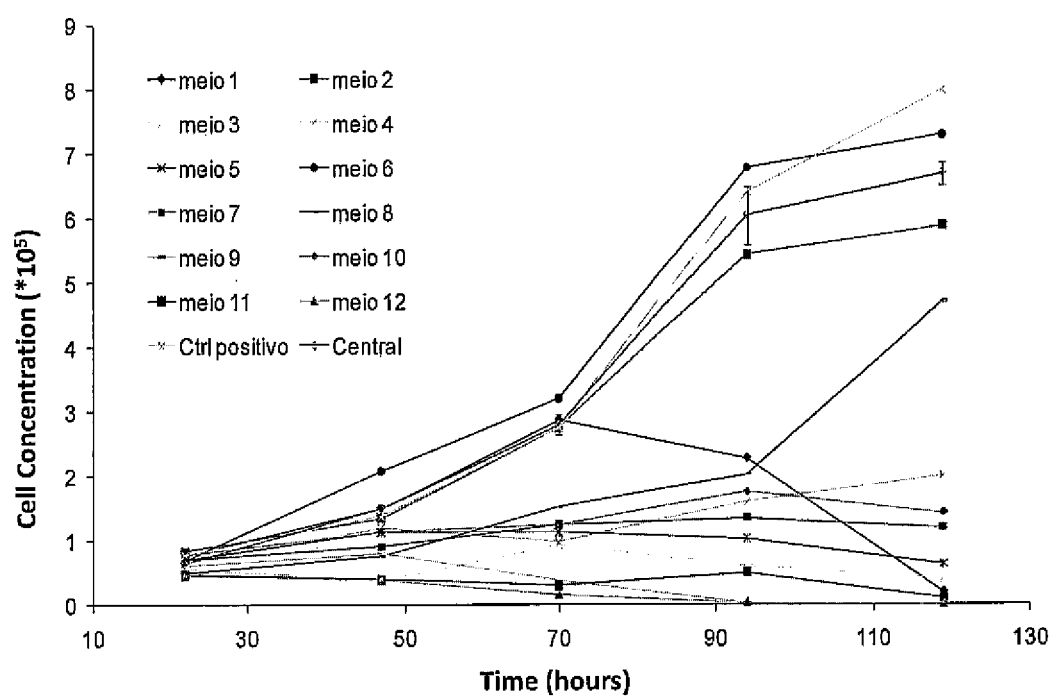
FIG. 1: Kinetic growth of H-9 cell lines culture on the different formulation created with the PB12 matrix, plus the positive control (made with KSR) and main central points.

All scientific and technical terms used in this application have meanings commonly used in the art unless otherwise specified. As used in this application, the following words or phrases have the meanings specified.

As used herein, "Free of animal or human derived proteins" means protein that is recombinantly synthesized, or chemically synthesized but not isolated from an animal/human biological sample.

As used herein, "Xeno-free" means that medium having no xenogeneic products in or from the culture system.

Essentially feeder-free means that the medium does not contain exogenously added conditioned medium taken from a culture of feeder cells or exogenously added feeder cells in the culture.

Depending on culture conditions, pluripotent stem cells can produce colonies of differentiated cells or undifferentiated cells. The term "differentiated" is a relative term describing a cell's progression down a developmental pathway in comparison with another cell. For example, a pluripotent cell can give rise to any cell of the body, while a more differentiated cell such as a hematopoietic cell will give rise to fewer cell types.

Cultures of pluripotent stem cells may be described as "undifferentiated" when a substantial proportion of stem cells and their derivatives in the population display morphological characteristics of undifferentiated cells and express undifferentiated markers such as Nanog, Oct-4 and SSEA-4. Undifferentiated stem cells (e.g., ES or iPS cells) are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

Culture Media of the Invention

The present invention provides defined low protein culture media for maintaining stein cells in an undifferentiated state. In accordance with the practice of the invention, the media is essentially feeder-free, essentially xeno-free, essentially free of beta-mercaptoethanol or other agents that break disulfide bonds such as dithiothreitol and tris(2-carboxyethyl)phosphine), and essentially free of animal-derived or human-derived proteins. In one embodiment, the medium is also essentially free of the contaminant sialic acid Neu5Gc (N-Glycolylneuraminic acid).

In one embodiment, the medium comprises a basal medium, an organic acid (e.g., an acid from the tricarboxylic acid cycle) or its equivalent, nonessential amino acids or its equivalent, a combination of growth factors or its equivalent including but not limited to a fibroblast growth factor (FGF) (e.g., FGF-2 protein), an insulin-like growth factor (IGF) (e.g., IGF-1 protein) or insulin, a transferrin protein, and a transforming growth factor (TGF) (e.g., TGF beta 1 protein) or its equivalent (e.g., Activin A). In one embodiment, the combination of growth factors consists of the four growth factors, FGF-2 protein, an IGF-1 protein or insulin, a Transferrin protein, and a TGF beta 1 protein. Additionally, the medium comprises a chemical based buffer, such as HEPES and/or sodium bicarbonate and/or its equivalents, a chemical-and-gas-based buffering system, such as bicarbonate-$CO_2$ buffering system, or a combination of both. The pH of the medium may be maintained by the chemical based buffer and/or the chemical-and-gas-based buffering system. In an embodiment of the invention, the basal medium is DMEM or DMEM/F12.

Examples of organic acids include, but are not limited to, citric acid, cis-aconitic acid, isocitiric acid, alpha-ketoglutaric acid, succinic acid, fumaric acid, malic acid, and oxalic acid, or mixtures thereof.

In another embodiment of this invention, the defined culture medium of the invention further comprise one, more or all of albumin, vitamin B, glutamine, Sodium Selenite and Chemically Defined Lipid concentrate (CDL) and a combination of hepes and sodium bicarbonate. Vitamin B may be in the form of a vitamin B stock solution comprising: thiamine, -i-inositol, riboflavin, pyridoxal, nicotinamide, folic acid, pantothenate and choline.

In yet another embodiment, the defined culture medium may further comprise one, more or all of a Pipecolic acid or a derivative or equivalent thereof, γ-aminobutyric acid (GABA) or a derivative or equivalent thereof, Albumin, and a combination of hepes and sodium bicarbonate.

The present invention also provides a defined low protein culture medium for maintaining cells in an undifferentiated state comprising a citric acid, Nonessential amino acids, glutamine, Chemically Defined Lipid concentrate (CDL), basic fibroblast growth factor (FGF-2), insulin-like growth factor 1 (IGF-1) or insulin, Transferrin, transforming growth factor beta 1 (TGF beta 1), Pipecolic acid, γ-aminobutyric acid (GABA), Albumin, and a combination of hepes and sodium bicarbonate.

In one embodiment of the defined culture medium, the organic acid (e.g., citric acid) may be present in the range of about 11.61 mg/L-14.19 mg/L, about 5.6 mg/L to 20.1 mg/L, about 4 mg/L-25 mg/L, about 10.9 mg/L-14.9 mg/L, about 10 mg/L-15 mg/L, or about 10.32-15.48 mg/L. The pH of medium may be in the range of about 7.2-7.5, 7.1-7.3 or 7.0-7.5. In a preferred embodiment, the amount of organic acid (e.g., citric acid) is about 12.9 mg/L.

In another embodiment of this invention, the amount of nonessential amino acids (volume/volume) may be in the range of about 1.75%-2.15% (v/v), about 1.0%-2.95% (v/v), about 0.5%-2.9% (v/v), about 0.75%-2.5% (v/v), about 1%-2% (v/v) or about 1.56%-2.34% (v/v). In a preferred embodiment, the amount nonessential amino acids is about 1.95% (volume/volume (v/v)).

In another embodiment of this invention, the amount of glutamine (or its equivalents, e.g., glutamax) may be in the range of about 4.05 mM 4.95 mM, about 2.5 mM-6.5 mM, about 3 mM-4 mM, about 4 mM 4.5 mM, about 4.5 mM-5 mM, about 2.75 mM-5 mM or about 3.6 mM 5.4 mM. In a preferred embodiment, the amount of glutamine is about 4.5 mM.

In another embodiment of this invention, the amount of CDL may be in the range of about 0.45%-0.55% (v/v), about 0.5%-1.0% (v/v), about 0.1%-1.0% (v/v), or about 0.4%-0.6% (v/v). In a preferred embodiment, the amount of CDL is about 0.5% (v/v).

In another embodiment of this invention, the amount of FGF (e.g., FGF-2) is in the range of about 54 ng/mL-66 ng/mL, about 0.1 ng/mL-200 ng/mL, about 60 ng/mL-100 ng/mL, about 40 ng/mL-70 ng/mL, about 1 ng/mL-200 ng/mL, about 1 ng/mL-100 ng/mL, about 8 ng/mL-100 ng/mL, about 10 ng/mL-90 ng/mL, about 10 ng/mL-80 ng/mL, about 40 ng/mL-70 ng/mL or about 48-72 ng/mL. In a preferred embodiment, the amount of FGF is about 60 ng/mL.

In another embodiment of this invention, the amount of IGF (e.g., IGF-1) may be in the range of about 216 ug/L-264 ug/L, about 50 ug/L-240 ug/L, about 100 ug/L 300 ug/L or about 192 ug/L-288 ug/L. In a preferred embodiment, the amount of IGF is about 250 ug/L.

In another embodiment of this invention, the amount of Transferrin may be in the range of about 10.8 mg/L-13.2 mg/L, about 0.1 mg/L-25 mg/L, about 2 mg/L-25 mg/L, about 5 mg/L-20 mg/L, or about 9.6 mg/L-14.4 mg/L. In a preferred embodiment, the amount of Transferrin is about 250 ug/L.

In another embodiment of this invention, the amount of TGF (e.g., TGF beta 1) is in the range of about 1.8 ng/mL-2.2 ng/mL, about 0.1 ng/mL-2 ng/L, about 0.2 ng/mL-2.5 ng/mL or about 1.6 ng/mL-2.4 ng/mL. In a preferred embodiment, the amount of TGF is about 2 ng/mL.

In another embodiment of this invention, the amount of Pipecolic acid may be in the range of about $8.86 \times 10^{-4}$ mM-$10.82 \times 10^{-4}$ mM, about $9.85 \times 10^{-4}$ nM or about $7.87 \times 10^{-4}$ mM-$11.81 \times 10^{-4}$ nM. In a preferred embodiment, the amount of Pipecolic acid is about $9.84 \times 10^{-4}$ mM.

In another embodiment of this invention, the amount of GABA is in the range of about $8.81 \times 10^{-1}$ mM-$10.77 \times 10^{-1}$ mM, about $7.83 \times 10^{-1}$ mM-$11.75 \times 10^{-1}$ mM or about $1.3 \times 10^{-3}$ mM-$0.7 \times 10^{-4}$ mM. In a preferred embodiment, the amount of GABA is about $9.79 \times 10^{-1}$ mM.

In another embodiment of this invention, the amount of albumin is in the range of about 0.36 g/L-0.44 g/L, about 0.1 g/L-8 g/L, about 0.3 g/L-0.5 g/L, about 0.2 g/L-0.6 g/L or about 0.32 g/L-0.48 g/L. In a preferred embodiment, the amount of albumin is about 0.4 g/L.

In another embodiment of this invention, the amount of the sodium bicarbonate may be in the range of 1.2 g/L 2.8 g/L, and the amount of HEPES may be in the range of 10 mM-18 mM.

In another embodiment of this invention, the amount of sodium selenite may be in the range of $0.81 \times 10^{-4}$ mM-$0.98 \times 10^{-4}$ mM, $0 \times 10^{-4}$ mM-$1.77 \times 10^{-4}$ mM, $0.71 \times 10^{-4}$ mM-$1.07 \times 10^{-4}$ mM or $0.62 \times 10^{-4}$ mM-$1.16 \times 10^{-4}$ mM.

In one embodiment of this invention, the medium comprises only four growth factors which are a FGF-2 protein, an IGF-1 protein or insulin, a Transferrin protein, and a TGF beta 1 protein.

In a further embodiment of this invention, the stein cells are human pluripotent stem cells and the stem cells are human embryonic stein cells or induced pluripotent stem cells.

The invention also provides a serum substitute comprising Citric Acid, Sodium Selenite, Nonessential amino acids, Glutamine, bFGF, recombinant albumin, recombinant transferrin and recombinant IGF-1.

METHODS OF THE INVENTION

The present invention provides methods for maintaining and expanding stem cells in an undifferentiated state in culture comprising culturing the stein cells in the defined low protein culture medium of the invention, but not co-cultured with feeder cells. In accordance with the practice of the invention, the medium of the invention is essentially feeder-free, essentially xeno-free, essentially free of any denaturing agents, essentially free of beta-mercaptoethanol or its equivalents and essentially free of animal-derived or human-derived proteins.

In one embodiment of this invention, the stem cells so cultured are grown in and fed by the defined culture medium which is replaced after about every 24-72 hours. In a further embodiment, the cells are passaged between 0 hours and 72 hours after reaching passing confluence.

In another embodiment of this invention, the stem cells are cultured on a matrix and the matrix is a polymer matrix. In one embodiment, the stem cells so cultured on the matrix are attached to the matrix.

In the methods of the invention, the stem cells are maintained in an undifferentiated state using media that is essentially feeder-free, essentially xeno-free, essentially free of beta-mercaptoethanol or other agents that break disulfide bonds such as dithiothreitol and tris(2-carboxyethyl)phosphine), and essentially free of animal-derived or human-derived proteins. In one embodiment, the medium is also free of the contaminant sialic acid Neu5Gc (N-Glycolyl-neuraminic acid).

In one embodiment, the method grows the stein cells in medium comprising a basal medium, an organic acid (e.g., an acid from the tricarboxylic acid cycle), nonessential amino acids, a combination of growth factors including but not limited to a fibroblast growth factor (FGF) (e.g., FGF-2 protein), an insulin-like growth factor (IGF) (e.g., IGF-1 protein) or insulin, a transferrin protein, and a transforming growth factor (TGF) (e.g., TGF beta 1 protein) or its equivalent (e.g., Activin A). In one embodiment, the combination of growth factors consists of the four growth factors, FGF-2 protein, an IGF-1 protein or insulin, a Transferrin protein, and a TGF beta 1 protein. Additionally, the medium may comprise a chemical based buffer, such as HEPES and/or sodium bicarbonate and/or its equivalents, a chemical-and-gas-based buffering system, such as bicarbonate-$CO_2$ buffering system, or a combination of both. The pH of the medium may be maintained by the chemical based buffer and/or the chemical-and-gas-based buffering system. In an embodiment of the invention, the basal medium of the defined culture medium is DMEM or DMEM/F12.

In one embodiment, the method provides growing the stein cells in a defined low 2.5 protein culture medium for maintaining cells in an undifferentiated state comprising a citric acid, Nonessential amino acids, glutamine, Chemically Defined Lipid concentrate (CDL), basic fibroblast growth factor (FGF-2), insulin-like growth factor 1 (IGF-1) or insulin, Transferrin, transforming growth factor beta 1 (TGF beta 1), Pipecolic acid, γ-aminobutyric acid (GABA), Albumin, and a combination of hepes and sodium bicarbonate.

In another embodiment of this invention, the stein cells are grown in the defined culture medium, wherein the organic acid (e.g., citric acid) may be present in the range of about 11.61 mg/L-14.19 mg/L, about 5.6 mg/L to 20.1 mg/L, about 4 mg/L-25 mg/L, about 10.9 mg/L-14.9 mg/L, about 10 mg/L-15 mg/L, or about 10.32-15.48 mg/L. The pH of medium may be in the range of about 7.2-7.5, 7.1-7.3 or 7.0-7.5. In a preferred embodiment, the amount of organic acid (e.g., citric acid) may be about 12.9 mg/L.

In yet another embodiment of this invention, the stem cells are grown in the defined culture medium, wherein the amount of nonessential amino acids (volume/volume) may be in the range of about 1.75%-2.15% (v/v), about 1.0%-2.95% (v/v), about 0.5%-2.9% (v/v), about 0.75%-2.5% (v/v), about 1%-2% (v/v) or about 1.56%-2.34% (v/v). In a preferred embodiment, the amount nonessential amino acids may be about 1.95% (volume/volume (v/v)).

In another embodiment of this invention, the stem cells are grown in the defined culture medium, wherein the amount of glutamine (or its equivalents, e.g., glutamax) may be in the range of about 4.05 mM-4.95 mM, about 2.5 mM-6.5 mM, about 3 mM-4 mM, about 4 mM-4.5 mM, about 4.5 mM-5 mM, about 2.75 mM-5 mM or about 3.6 mM-5.4 mM. In a preferred embodiment, the amount of glutamine is about 4.5 mM.

In another embodiment of this invention, the stein cells are grown in the defined culture medium, wherein the amount of CDL may be in the range of about 0.45%-0.55% (v/v), about 0.5%-1.0% (v/v), about 0.1%-1.0% (v/v), or about 0.4%-0.6% (v/v). In a preferred embodiment, the amount of CDL may be about 0.5% (v/v).

In another embodiment of this invention, the stem cells are grown in the defined culture medium, wherein the amount of FGF (e.g., FGF-2) is in the range of about 54 ng/mL-66 ng/mL, about 0.1 ng/mL-200 ng/mL, about 60 ng/mL-100 ng/mL, about 40 ng/mL-70 ng/mL, about 1 ng/mL-200 ng/mL, about 1 ng/mL-100 ng/mL, about 8 ng/mL-100 ng/mL, about 10 ng/mL-90 ng/mL, about 10 ng/mL-80 ng/mL, about 40 ng/mL-70 ng/mL or about 48-72 ng/mL. In a preferred embodiment, the amount of FGF may be about 60 ng/mL.

In another embodiment of this invention, the stem cells are grown in the defined culture medium, wherein the amount of IGF (e.g., IGF-1) may be in the range of about 216 ug/L-264 ug/L, about 50 ug/L-240 ug/L, about 100 ug/L-300 ug/L or about 192 ug/L-288 ug/L, In a preferred embodiment, the amount of IGF may be about 250 ug/L.

In another embodiment of this invention, the stem cells are grown in the defined culture medium, wherein the amount of Transferrin may be in the range of about 10.8 mg/L-13.2 mg/L, about 0.1 mg/L-25 mg/L, about 2 mg/L-25 mg/L, about 5 mg/L-20 mg/L, or about 9.6 mg/L-14.4 mg/L. In a preferred embodiment, the amount of Transferrin may be about 250 ug/L.

In another embodiment of this invention, the stem cells are grown in the defined culture medium, wherein the amount of TGF (e.g., TGF beta 1) is in the range of about 1.8 ng/mL-2.2 ng/mL, about 0.1 ng/mL-2 ng/L, about 0.2 ng/mL-2.5 ng/mL or about 1.6 ng/mL-2.4 ng/mL. In a preferred embodiment, the amount of TGF may be about 2 ng/mL.

In another embodiment of this invention, the stem cells are grown in the defined culture medium, wherein the amount of Pipecolic acid may be in the range of about $8.86 \times 10^{-4}$ mM-$10.82 \times 10^{-4}$ mM, about $9.85 \times 10^{-4}$ nM or about $7.87 \times 10^{-4}$ mM-$11.81 \times 10^{-4}$ nM. In a preferred embodiment, the amount of Pipecolic acid may be about $9.84 \times 10^{-4}$ mM.

In another embodiment of this invention, the stem cells are grown in the defined culture medium, wherein the amount of GABA is in the range of about $8.81 \times 10^{-1}$ mM-$10.77 \times 10^{-1}$ mM, about $7.83 \times 10^{-1}$ mM-$11.75 \times 10^{-1}$ mM or about $1.3 \times 10^{-3}$ mM-$0.7 \times 10^{-4}$ mM. In a preferred embodiment, the amount of GABA may be about $9.79 \times 10^{-1}$ mM.

In another embodiment of this invention, the stem cells are grown in the defined culture medium, wherein the amount of albumin is in the range of about 0.36 g/L 0.44 g/L, about 0.1 g/L-8 g/L, about 0.3 g/L-0.5 g/L, about 0.2 g/L-0.6 g/L or about 0.32 g/L-0.48 g/L. In a preferred embodiment, the amount of albumin may be about 0.4 g/L.

In another embodiment of this invention, the stem cells are grown in the defined culture medium, wherein the amount of the sodium bicarbonate may be in the range of 1.2 g/L-2.8 g/L, and the amount of HEPES may be in the range of 10 mM-18 mM.

In another embodiment of this invention, the stem cells are grown in the defined culture medium, wherein the amount of sodium selenite may be in the range of $0.81 \times 10^{-4}$ mM-$0.98 \times 10^{-4}$ mM, $0 \times 10^{-4}$ mM-$1.77 \times 10^{-4}$ mM, $0.71 \times 10^{-4}$ mM-$1.07 \times 10^{-4}$ mM or $0.62 \times 10^{-4}$ mM-$1.16 \times 10^{-4}$ mM.

Advantages of the Invention

This invention provides media formulations with the desired biological functions and that may be (1) defined, (2) xeno-free, and (3) cost effective. Additionally, in an embodiment of the invention, the medium (MaSeR2) was designed to be more cost attractive compared to the current media on the market, and is the only clinical-grade media that can be used for hES and iPS cell based therapies since it has no trace of animal contaminates, and sialic acid Neu5Gc (N-Glycolylneuraminic acid). Neu5Gc can be metabolically incorporated into the surface of cultured cells. Most humans have antibodies to Neu5Gc from dietary sources such as milk and beef. The incorporation of nonhuman Neu5Gc into the cell surface of hSEC or hiPSC can potentially evoke undesirable immune responses from the host and compromise the efficacy and safety of cell based therapies.

By not using feeder cells, the media in combination with defined matrix can truly offer xeno-free, and defined culture condition for stem cells like hSEC and hiPSC.

Additionally, in one embodiment, the invention provides the following advantage, namely, it is essentially free of beta-mercaptoethanol (BME). It is clear that even in very small concentration (20 μM) BME have a statistically negative effect on ES cell growth for low protein amount formulation (p<0.01, t-test). Astonishingly, BME is normally added and recommended in KSR based media and feeder free media like mTeSR1 and StemPro. However, the negative effect of this compound is probably buffered by the increased amount of proteins in current media, around 10 grams per liter, while the invention provides at least about 20 times less. This discovery represents a breakthrough in terms of identifying the real growth needs of a stem cell, thereby drastically changing what media is needed and identifying the cell's optimal growing environment.

Another aspect of the invention provides a new media formulation from a classic basal media (DMEM/F12 mixture 1:1) which is capable of supporting the culture of hES and iPS cells in feeder-free scenarios in a pluripotency state. Moreover, the formula is optimized for the culture of hES and iPS cells. Specifically, for the first time, the effect of each component was evaluated and measured through a robust mathematical model, leading to a formulation where each component is working at its optimal concentration.

Additionally, through several optimization steps, many compounds that are currently being used in common feeder (KSR-based) and feeder-free (mTeSR1) media were found to be unnecessary and at times even inhibitory for cell growth performance.

Furthermore, interactions between the selected factors were discovered resulting in a scenario where the synergy between them was enhanced.

The following examples are presented to illustrate the present invention and to assist one of ordinary skill in making and using the same. The examples are not intended in any way to otherwise limit the scope of the invention.

EXAMPLES

Example 1

To develop a media with no animal product in its formulation, the first series of experiments were designed to replace fetal bovine serum (FBS) and Knockout Serum Replacement (KSR) (Invitrogen) with a chemically defined and xeno-free serum substitute, while still using a feeder layer.

Supplements were added to a chemically defined medium Dulbecco's Modification of Eagle's Medium (DMEM)/Ham's F-12 50/50 Mix (DMEM/F12; Mediatech, Manassas, Va.; catalog number 10-092) that does not contain FBS or has a diminished amount of it. As mentioned, since KSR does not have an available formulation, the criteria for the selection of the supplements that would replace it was the same used for the substitution of FBS.

Initially, eight different supplements were chosen: CellPrime rAlbumin AF-S-recombinant human albumin (Millipore, Billerica, Mass.; catalog number 9501), CellPrime™ rTransferrin AF-recombinant human transferrin (Millipore, Billerica, Mass.; catalog number 9701), non-essential amino acids (NEAA; Invitrogen, Carlsbad, Calif.; catalog number 11140035), glutamine (Invitrogen, Carlsbad, Calif.; catalog number 25030-149), sodium selenite (Sigma-Aldrich, St. Louis, Mo.; catalog number S5261), citric acid (Sigma-Aldrich, St. Louis, Mo.; catalog number C2404), ethanolamine (Sigma-Aldrich, St. Louis, Mo.; catalog number E0135) and Long R3 IGF-I human-modified recombinant human insulin-like growth factor (Sigma-Aldrich, St. Louis, Mo.; catalog number 85580C).

Unless otherwise indicated, all supplements were either resuspended or reconstituted following the direction of the manufacturer. Phosphate buffered saline (PBS) was used to resuspend albumin, sodium selenite, citric acid, and FGF-2. Acetic acid (10 mM) was used to resuspend IGF-1 and citric acid for TGF-beta-1. Transferrin, CDL, and NEAA are provided in a liquid form.

A Placket-Burman matrix of 12 independent conditions (PB12) was used (Table 1), according to the Design of Experiments (DOE) methodology for the screening of 8 factors (RODRIGUES & IEMMA, 2005). Three different levels are evaluated according to this methodology:

Level +1: represents the highest value from the range evaluated. +1 condition, or in other words, the maximum concentration of each factor, was set according to current literature or manufacture's suggestion (Table 2).

Level −1: represents the lowest value. Since this first step, the PB12, is a screening step, whenever it was possible the concentration of the factor was set as zero.

Condition 0: represents the central condition of the DOE, being the mean value obtained from averaging the values for levels −1 and +1. In addition to the central condition, the "main" central condition is defined as a state when all factors are set to condition 0.

In total, 14 different conditions were examined: 12 related to the PB12 matrix, 1 related to the "main" central condition that was performed in quadruplicates for the error estimation and a control condition with KSR. The basal media was: a 1:1 mixture 1:1 of DMEM and Ham's F12 (DMEM/F12; Mediatech, Manassas, Va.; catalog number 10-092), 1% NEAA, 110 μM β-mercaptoethanol (BME; Sigma-Aldrich, St. Louis, Mo.; catalog number M7522), 50 μg/mL gentamicin sulfate (Mediatech, Manassas, Va.; catalog number 30-005-CR) and 8 ng/mL of FGF-2 (Peprotech, Rocky Hill, N.J.; catalog number 100-18B). FGF-2 was reconstituted in PBS at 100 ug/mL and was added to the media for a final concentration of 8 ng/mL at the start of the culture. During the culture period, additional FGF-2 (8 ng/mL) was added directly to the media on a daily basis.

TABLE 1

PB12 matrix and "main" central condition, performed in quadruplicate, used to analyze the contribution of 8 different media supplements. The matrix and "main" central condition represent 13 distinct new formulations.

| PB12 | Album. | NEAA | Transf. | Selenium | Citr. Ac. | Etan. | Glut. | IGF-1 |
|---|---|---|---|---|---|---|---|---|
| 1 | 1 | −1 | 1 | −1 | −1 | −1 | 1 | 1 |
| 2 | 1 | 1 | −1 | 1 | −1 | −1 | −1 | 1 |
| 3 | −1 | 1 | 1 | −1 | 1 | −1 | −1 | −1 |
| 4 | 1 | −1 | 1 | 1 | −1 | 1 | −1 | 1 |
| 5 | 1 | 1 | −1 | 1 | 1 | −1 | 1 | 1 |
| 6 | 1 | 1 | 1 | −1 | 1 | 1 | −1 | 1 |
| 7 | −1 | 1 | 1 | 1 | −1 | 1 | 1 | −1 |
| 8 | −1 | −1 | 1 | 1 | 1 | −1 | 1 | 1 |
| 9 | −1 | −1 | −1 | 1 | 1 | 1 | −1 | 1 |
| 10 | 1 | −1 | −1 | −1 | 1 | 1 | 1 | −1 |
| 11 | −1 | 1 | −1 | −1 | −1 | 1 | 1 | 1 |
| 12 | −1 | −1 | −1 | −1 | −1 | −1 | −1 | −1 |
| 13 | 0 | 0 | 0 | 0 | 0 | 0 | 0 | 0 |
| 13 | 0 | 0 | 0 | 0 | 0 | 0 | 0 | 0 |
| 13 | 0 | 0 | 0 | 0 | 0 | 0 | 0 | 0 |
| 13 | 0 | 0 | 0 | 0 | 0 | 0 | 0 | 0 |

TABLE 2

Range of concentration for the supplements analyzed in the P12 matrix.

| Factor | Range Evaluated |
|---|---|
| Albumin | 0-12 g/L |
| NEAA | 1-2% |
| Transferrin | 0-10 mg/L |
| Sodium selenite | 0-1.77 × 10$^{-4}$ mM |
| Citric Acid | 0-0.01692 g/L |
| Ethanolamine | 0-0.003054 g/L |
| Glutamine | 2.5-6.5 mM |
| IGF-1 | 50-100 ug/L |

In order to perform the experiment, H-9 cells were inoculated homogenously, as suggested by the current feeder protocols, in 5 wells (3.6 cm$^2$) for each one of the 13 conditions and 20 wells (quadruplicates) for the main central condition. Every 24 hours one well from each condition and 4 wells from the main central condition were enzymatic dissociated and counted with the help of an automatic counter (NucleoCounter NC-100), for an unbiased measure of cell growth. In that way, by the end of the 5 days, a kinetic curve was obtained for every single condition (FIG. 1). Readouts like integral of cells (integral; defined as area below the curve), maximum productivity (Px,max; defined as the highest value obtained from dividing cell number by time) or and specific global ( ) growth rate (or speed of cell growth obtained from the formula $dX/dt=pX$) were calculated in order to perform the statistics comparing all different curves (Table 3).

TABLE 3

Readouts calculated from the kinetic curves of the PB12.

| Formulation | Integral (10$^5$ cells h) | μ (h$^{-1}$) | Px, max (10$^5$ cells h$^{-1}$) |
|---|---|---|---|
| 1 | 171 | −0.0136 | 0.044 |
| 2 | 313 | 0.0202 | 0.063 |
| 3 | 57 | −0.0032 | 0.007 |
| 4 | 124 | 0.0115 | 0.022 |
| 5 | 95 | −0.0011 | 0.017 |
| 6 | 390 | 0.0245 | 0.084 |
| 7 | 107 | 0.0055 | 0.011 |
| 8 | 168 | 0.0231 | 0.043 |
| 9 | 36 | −0.0327 | 0.008 |
| 10 | 126 | 0.0062 | 0.014 |
| 11 | 36 | −0.0160 | 0.000 |
| 12 | 18 | −0.0297 | −0.003 |
| 13 | 329 | 0.0252 | 0.069 |
| 13 | 347 | 0.0237 | 0.078 |
| 13 | 346 | 0.0224 | 0.080 |
| 13 | 340 | 0.0256 | 0.071 |
| Ctrl+ | 363 | 0.0240 | 0.078 |

Observing the Table 3 and the FIG. 1, it is clear that some conditions created by the P12 matrix are similar in performance as the positive control made with KSR.

In order to statistically evaluate the effect and the significance of each factor to the calculated readouts, the Statistica software (7.0 version) was used and the ANOVA table shows each supplement influence each readout according to its p-value (Table 4).

TABLE 4

Effects, errors, calculated t, p-value and minimum/maximum limits of each parameter were estimated for every readout (Integral, Px, max and μ) related to PB12. Statistically relevant effects (p < 0.1) are bolded.

| | Effect | Error | t (3) | p-value | Min (90% conf) | Max (90% conf) |
|---|---|---|---|---|---|---|
| Integral | | | | | | |
| Mean | 188.04 | 2.09 | 89.94 | 0.000003 | 183.12 | 192.96 |
| Albumin | 132.76 | 4.83 | 27.50 | 0.000106 | 121.40 | 144.13 |
| NEAA | 59.18 | 4.83 | 12.26 | 0.001170 | 47.81 | 70.54 |
| Transf. | 65.44 | 4.83 | 13.55 | 0.000869 | 54.07 | 76.80 |
| Selenite | 7.46 | 4.83 | 1.55 | 0.220049 | −3.90 | 18.82 |
| Citric Acid | 17.09 | 4.83 | 3.54 | 0.038362 | 5.73 | 28.46 |
| Etan. | −0.56 | 4.83 | −0.12 | 0.915566 | −11.92 | 10.81 |
| Glut | −39.15 | 4.83 | −8.11 | 0.003921 | −50.52 | −27.79 |
| IGF-1 | 97.69 | 4.83 | 20.23 | 0.000264 | 86.32 | 109.05 |
| Px, max | | | | | | |
| Mean | 0.0383 | 0.0013 | 29.32 | 0.000087 | 0.0353 | 0.0414 |
| Albumin | 0.0297 | 0.0030 | 9.82 | 0.002243 | 0.0226 | 0.0368 |
| NEAA | 0.0094 | 0.0030 | 3.13 | 0.052183 | 0.0023 | 0.0165 |
| Transf. | 0.0189 | 0.0030 | 6.25 | 0.008247 | 0.0118 | 0.0260 |
| Selenite | 0.0029 | 0.0030 | 0.97 | 0.405524 | −0.0042 | 0.0100 |
| Citric Acid | 0.0060 | 0.0030 | 1.98 | 0.142111 | −0.0011 | 0.0131 |
| Etan. | −0.0055 | 0.0030 | −1.81 | 0.168471 | −0.0126 | 0.0016 |
| Glut | −0.0088 | 0.0030 | −2.93 | 0.061110 | −0.0159 | −0.0017 |
| IGF-1 | 0.0292 | 0.0030 | 9.67 | 0.002346 | 0.0221 | 0.0363 |
| μ | | | | | | |
| Mean | 0.0057 | 0.0004 | 15.58 | 0.000574 | 0.0049 | 0.0066 |
| Albumin | 0.0168 | 0.0008 | 19.83 | 0.000280 | 0.0148 | 0.0188 |
| NEAA | 0.0108 | 0.0008 | 12.76 | 0.001039 | 0.0088 | 0.0128 |
| Transf. | 0.0169 | 0.0008 | 19.84 | 0.000280 | 0.0149 | 0.0189 |
| Selenite | 0.0098 | 0.0008 | 11.49 | 0.001416 | 0.0078 | 0.0118 |
| Citric Acid | 0.0065 | 0.0008 | 7.61 | 0.004708 | 0.0045 | 0.0085 |
| Etan. | 0.0006 | 0.0008 | 0.71 | 0.526236 | −0.0014 | 0.0026 |
| Glut | 0.0023 | 0.0008 | 2.67 | 0.075925 | 0.0003 | 0.0043 |
| IGF-1 | 0.0027 | 0.0008 | 3.18 | 0.049963 | 0.0007 | 0.0047 |

Through the estimation of the effects from the least square method and the calculation of the errors obtained by the replicates performed on the main central condition (formulation 13), "t" was calculated as the ratio of effect and error.

By comparing the calculated "t" value with "t" values from a Student's "t" distribution table for a bilateral distribution, the p-value was obtained for each parameter in every readout. A priori, establishing a confidence interval of 90%, it is possible to identify, on Table 4, statistically significant (bolded) effect of a supplement on the Integral, Px,max and μ readout.

It is noted that most of the supplements seem to have some influence, positive or negative, on the readouts evaluated, demonstrating that the group of factors chosen as a replacement for KSR behaved similarly. Since PB matrix designs contain many variables for few conditions, a conservative posture was adopted that no supplement is to be discarded from the list of supplements unless the supplement is shown to be statistically not significant in all 3 readouts.

In that sense, the only factor that does not have any statistical relevance in all 3 readouts was the ethanolamine, and for that reason, it was discarded from future optimizations. Other components, like sodium selenite, citric acid and glutamine, had variable results, not showing statistical, significance or positive effects in some readouts. Therefore, these components were maintained at the central condition value, until future analysis. The only factors that had positive effect on all 3 readouts were the recombinant proteins and NEAA.

Representing over 95% of costs and almost 70% of positive effect in all readouts, the recombinant proteins were chosen for the initial step of optimization, and the NEAA were kept at central condition, for now.

Aiming to understand better the contribution of each protein in the formulation of the media, an optimization step was performed using the Three-Variable Rotatable Central Composite Design (RCCD; Rodrigues and lemma, 2005). The concentration range of each supplement was the same as given in Table 2 for the PB12 design, with the same concentration for the level 0, −1, and +1 condition. Remeasurement at these levels provided further confidence to the previously measured results. In addition, two more levels, −1.68 and +1.68, were included to increase the number of measurements as recommended by the RCCD methodology.

TABLE 5

3-Var RCCD table, representing 14 different conditions plus the "main" central condition. The codified values (+1.68, +1, 0, −1 and −1.68) of the matrix are labeled below the design, for each variable.

| DCCR | albumin | transferrin | IGF-1 |
|---|---|---|---|
| 1 | +1 | +1 | +1 |
| 2 | +1 | +1 | −1 |
| 3 | +1 | −1 | +1 |
| 4 | +1 | −1 | −1 |
| 5 | −1 | +1 | +1 |
| 6 | −1 | +1 | −1 |
| 7 | −1 | −1 | +1 |
| 8 | −1 | −1 | −1 |
| 9 | +1.68 | 0 | 0 |
| 10 | −1.68 | 0 | 0 |
| 11 | 0 | +1.68 | 0 |
| 12 | 0 | −1.68 | 0 |
| 13 | 0 | 0 | +1.68 |
| 14 | 0 | 0 | −1.68 |
| 15 | 0 | 0 | 0 |
| +1.68 | 12 g/L | 10 mg/L | 100 ug/L |
| +1 | 9.57 g/L | 7.97 mg/L | 79.7 ug/L |
| 0 | 6 g/L | 5 mg/L | 50 ug/L |
| −1 | 2.43 g/L | 2.03 mg/L | 20.3 ug/L |
| −1.68 | 0 g/L | 0 mg/L | 0 ug/L |

The basal media was: a 1:1 mixture 1:1 of DMEM and Ham's F12 (DMEM/F12; Mediatech, Manassas, Va.; catalog number 10-092), 1.5% NEAA, 8.46 mg/L citric acid, $0.89 \times 10^{-4}$ mM sodium selenite, 2 mM glutamine (total of 4.5 mM), BME 110 μM, gentamicin sulfate 50 μg/mL and 8 ng/mL of FGF-2.

As before, kinetics growth of H-9 cells were obtained and readouts like Integral and Px, max were calculated (Table 6).

By this time, the specific global (μ) growth rate was not calculated anymore, since its calculation principle relies on an exponential growth of the cells and many of the formulations did not produce a growth response permitting a proper curve fitting and this readout was no longer used in our comparisons.

TABLE 6

Readouts calculated from the kinetic curves of the first RCCD for recombinant proteins.

| Formulation | Integral ($10^5$ cells h) | Px,Max ($10^5$ cells h$^{-1}$) |
|---|---|---|
| 1 | 348 | 0.0743 |
| 2 | 338 | 0.0596 |
| 3 | 301 | 0.0596 |
| 4 | 287 | 0.0551 |
| 5 | 276 | 0.0660 |
| 6 | 151 | 0.0412 |
| 7 | 219 | 0.0505 |
| 8 | 117 | 0.0217 |
| 9 | 350 | 0.0826 |
| 10 | 38 | −0.0013 |
| 11 | 339 | 0.0794 |
| 12 | 100 | 0.0250 |
| 13 | 305 | 0.0618 |
| 14 | 104 | 0.0065 |
| 15 | 240 | 0.0524 |
| 15 | 245 | 0.0548 |
| 15 | 230 | 0.0484 |
| 15 | 239 | 0.0503 |
| Ctrl+ | 378 | 0.0939 |

The results in Table 6 support the conclusion obtained from the PB12 matrix that the protein supplements are important contributors to the growth in the defined media. The readout values were lowest when at least one of the three protein supplement was absent (condition 10, 12, and 14) or very low amount of the supplements was used (condition 8). Conversely, the readout values were in the high range when the higher concentration of the protein supplements were present. Thus, the $1^{st}$ RCCD optimization experiment supports the earlier conclusion of the importance of protein supplements obtained from the PB12 matrix experiment.

Through the use of Statistica software (StatSoft, Tulsa, Okla.), a second order mathematical model was generated in order to evaluate the real contribution of each supplement (Table 7).

TABLE 7

Table of regression from the 1st RCCD. Coefficient, errors, t, p-value and minimum/maximum limits of each parameter were estimated for every readout (Integral and Px, max). Statistically relevant effects (p < 0.1) are bolded. $R^2$ = 86.4% for Integral and 80.0% for Px, max.

| | Coefficient | Error | t (3) | p-value | Min (90% conf) | Max (90% conf) |
|---|---|---|---|---|---|---|
| integral | | | | | | |
| Mean | 236.27 | 3.10 | 76.27 | 0.000005 | 228.98 | 243.56 |
| Alb. (Linear) | 75.95 | 1.68 | 45.24 | 0.000024 | 72.00 | 79.90 |
| Alb. (Quadratic) | −4.80 | 1.74 | −2.75 | 0.070763 | −8.90 | −0.69 |

TABLE 7-continued

Table of regression from the 1st RCCD. Coefficient, errors, t, p-value and minimum/maximum limits of each parameter were estimated for every readout (Integral and Px, max). Statistically relevant effects (p < 0.1) are bolded. $R^2$ = 86.4% for Integral and 80.0% for Px, max.

|  | Coefficient | Error | t (3) | p-value | Min (90% conf) | Max (90% conf) |
|---|---|---|---|---|---|---|
| Transf. (Linear) | 43.29 | 1.68 | 25.79 | 0.000128 | 39.34 | 47.24 |
| Transf.(Quadratic) | 4.06 | 1.74 | 2.33 | 0.102471 | −0.05 | 8.16 |
| IGF-1 (Linear) | 42.99 | 1.68 | 25.60 | 0.000131 | 39.03 | 46.94 |
| IGF-1 (Quadratic) | −1.19 | 1.74 | −0.68 | 0.543929 | −5.30 | 2.91 |
| Alb. × Transf. | 0.88 | 2.19 | 0.40 | 0.713842 | −4.28 | 6.05 |
| Alb. × IGF-1 | −25.44 | 2.19 | −11.60 | 0.001377 | −30.60 | −20.27 |
| Transf. × IGF-1 | 2.25 | 2.19 | 1.03 | 0.380793 | −2.91 | 7.41 |
| Px, max |  |  |  |  |  |  |
| Mean | 0.0509 | 0.0014 | 36.86 | 0.000044 | 0.0477 | 0.0542 |
| Alb. (Linear) | 0.0154 | 0.0007 | 20.59 | 0.000251 | 0.0136 | 0.0172 |
| Alb. (Quadratic) | −0.0013 | 0.0008 | −1.66 | 0.195822 | −0.0031 | 0.0005 |
| Transf. (Linear) | 0.0107 | 0.0007 | 14.26 | 0.000747 | 0.0089 | 0.0124 |
| Transf.(Quadratic) | 0.0028 | 0.0008 | 3.60 | 0.036716 | 0.0010 | 0.0046 |
| IGF-1 (Linear) | 0.0121 | 0.0007 | 16.23 | 0.000509 | 0.0104 | 0.0139 |
| IGF-1 (Quadratic) | −0.0036 | 0.0008 | −4.61 | 0.019197 | −0.0054 | −0.0018 |
| Alb. × Transf. | −0.0020 | 0.0010 | −2.02 | 0.137109 | −0.0043 | 0.0003 |
| Alb. × IGF-1 | −0.0043 | 0.0010 | −4.41 | 0.021643 | −0.0066 | −0.0020 |
| Transf. × IGF-1 | 0.0008 | 0.0010 | 0.79 | 0.489170 | −0.0015 | 0.0031 |

The models shown on Table 7 can be statistically summarize into the equations 1 and 2. The very good correlation ($R^2$) (86.4% for integral and 80.0 for Px,max) indicates a decent concordance between the experimental values and the ones predicted by the mathematical model. Consequently, integral and Px,max vary according to the equations below:

$$\text{Integral} = 236.3 + 76.0A - 4.8A^2 + 43.3T + 43.0I - 25.4AI \quad \text{Eq. 1}$$

$$Px,\text{max} = 10^{-3}(50.9 + 15.4A + 10.7T + 2.8T^2 + 12.1I - 3.6I^2 - 4.3AI) \quad \text{Eq. 2}$$

(A is the value of the albumin, T is the value of transferrin and I is the value of IGF-1—codified values.)

Figure 2:
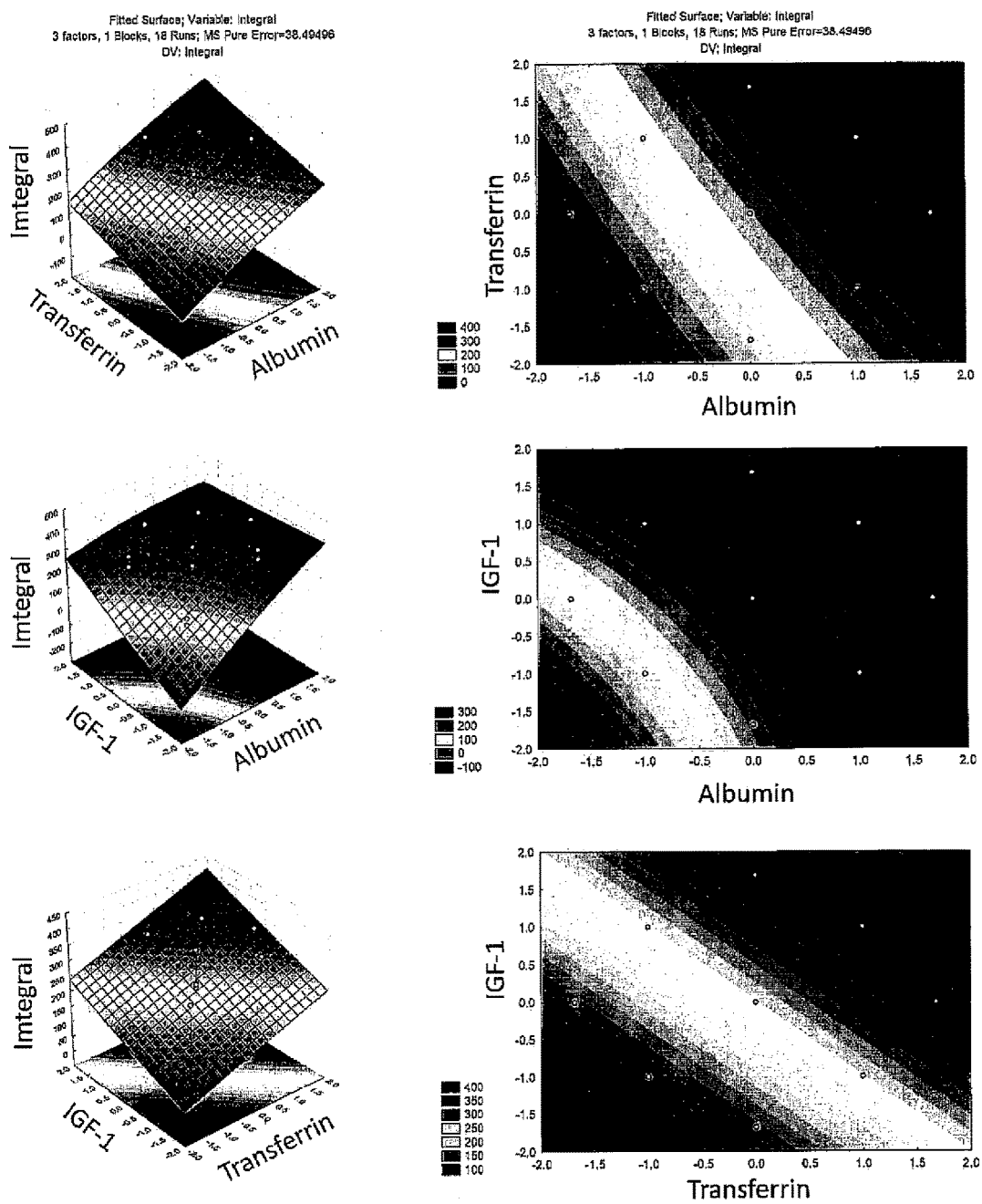
FIG. 2: Surface response and level curves, for integral, made through the model obtained on the 1st RCCD for recombinant proteins. In each graphic, the missing variable is at the central condition.
Figure 3:
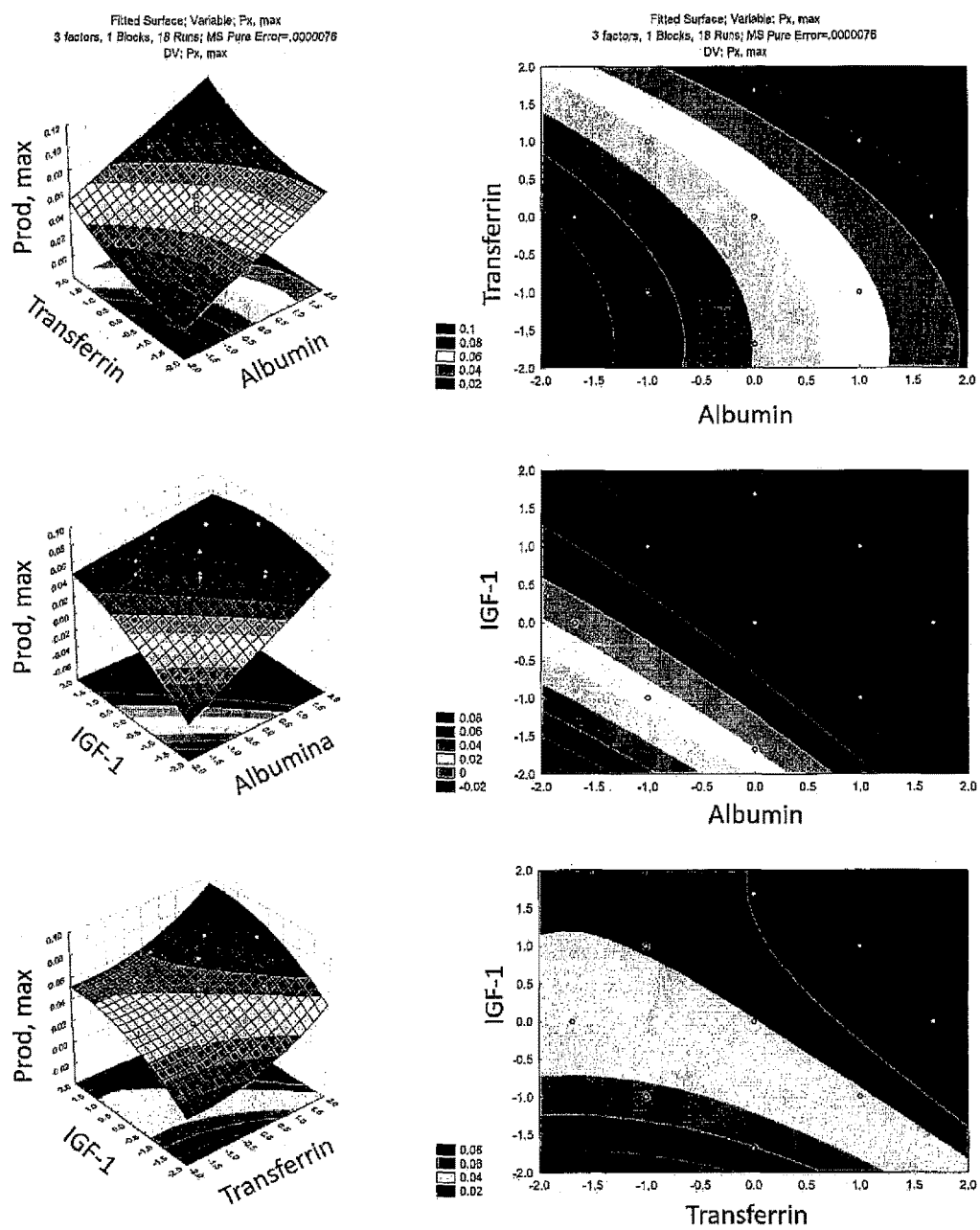
FIG. 3: Surface response and level curves, for Px,max, made through the model obtained on the 1st RCCD for recombinant proteins. In each graphic, the missing variable is at the central condition.

Carefully analyzing each equation makes possible to see the real contribution of each protein. As predicted by the raw data, the importance of the proteins is mathematically predicted in the equation by a very high value linear parameter. To better see these conclusions, all equations were plotted in "2 variable versus 1 readout way" where the third variable was fixed at the central condition. This result in 3 surfaces response or 3 level curves for each variable (FIG. 2 and FIG. 3).

Keeping in mind the surfaces produced by the equations, it is noticeable that the conditions which give a best readout value, meaning a better cell growth, are the ones with the maximum concentration of each variable. However, working in maximum ranges result in formulations that cost thousands per liter, making the new media unfeasible economically.

With the strong negative interaction between albumin and IGF-1, on conditions where one is maximized and other minimized, the model predicted excellent value of readouts.

Therefore, a new step of optimization was performed for a more cost-effective purpose, keeping one more expensive protein at a lower range and the less expensive one at a higher range. Since the recombinant albumin used is 30 times more expensive, its concentration was reduced, while the concentration of the cheaper recombinant IGF-1 was increased. Since the recombinant transferrin just showed positive effects with no interactions, the range at which this protein was evaluated was toward the higher concentration level to see if increases in IGF-1 concentration would produce a better performing media.

The same approach using a 3 variable (albumin, transferrin and IGF-1) RCCD was used (Table 5), however setting new concentration ranges for the five levels (Table 8).

TABLE 7

Concentration ranges and equivalent costs for each protein in the $2^{nd}$ RCCD.

| 2nd RCCD | albumin | US/L | transferrin | US/L | IGF-1 | US/L |
|---|---|---|---|---|---|---|
| +1.68 | 6.6 g/L | 2970 | 20 mg/L | 38 | 160 μg/L | 43 |
| +1 | 5.1 g/L | 2295 | 17.9 mg/L | 34 | 139 μg/L | 38 |
| 0 | 3.3 g/L | 1485 | 15 mg/L | 28 | 110 μg/L | 30 |
| −1 | 1.5 g/L | 675 | 12.1 mg/L | 23 | 81 μg/L | 22 |
| −1.69 | 0.6 g/L | 270 | 10 mg/L | 19 | 60 μg/L | 16 |

For the basal media, in order to add the 3 proteins mentioned above, we used a mixture 1:1 of DMEM and Ham's F12 plus: 1.5% NEAA, 8.46 mg/L citric acid, 0.89× $10^{-4}$ mM sodium selenite, 2 mM glutamine (total of 4.5 mM), BME 55 μM, gentamycin sulfate 50 μg/mL and 8 ng/mL of FGF-2.

Using the kinetics curve profile obtained with H-9 cells, Integral and Px,max were calculated for the $2^{nd}$ RCCD (Table 9).

TABLE 9

Readouts calculated from the kinetic curves of the second RCCD for recombinant proteins.

| Formulation | Integral ($10^5$ cells h) | Px, Max ($10^5$ cells h$^{-1}$) |
|---|---|---|
| 1 | 621 | 0.1660 |
| 2 | 589 | 0.1675 |
| 3 | 605 | 0.1791 |
| 4 | 577 | 0.1691 |
| 5 | 602 | 0.1675 |
| 6 | 560 | 0.1675 |
| 7 | 626 | 0.1938 |
| 8 | 547 | 0.1784 |
| 9 | 630 | 0.1652 |
| 10 | 558 | 0.1490 |

TABLE 9-continued

Readouts calculated from the kinetic curves of the second RCCD for recombinant proteins.

| Formulation | Integral ($10^5$ cells h) | Px, Max ($10^5$ cells h$^{-1}$) |
|---|---|---|
| 11 | 680 | 0.2031 |
| 12 | 538 | 0.1505 |
| 13 | 595 | 0.1791 |
| 14 | 565 | 0.1760 |
| 15 | 577 | 0.1892 |
| 15 | 609 | 0.1861 |
| 15 | 590 | 0.1830 |
| 15 | 586 | 0.1745 |
| Ctrl+ | 207 | 0.0608 |

Surprisingly, any condition performed was almost 3 times better than the positive control, made with KSR. Aiming to understand better the contribution of each protein in this new range, a mathematical model was created (Table 10).

TABLE 10

Table of regression from the 2nd RCCD. Coefficient, errors, t, p-value and minimum/maximum limits of each parameter were estimated for every readout (Integral and Px, max). Statistically relevant effects (p < 0.1) are bolded. $R^2$ = 62.7% for Integral and 37.9% for Px, max.

| | Coefficient | Error | t (3) | p-value | Min (90% conf) | Max (90% conf) |
|---|---|---|---|---|---|---|
| integral | | | | | | |
| Mean | 590.82 | 6.78 | 87.17 | 0.000003 | 574.87 | 606.77 |
| Alb. (Linear) | 12.93 | 3.67 | 3.52 | 0.038881 | 4.29 | 21.58 |
| Alb. (Quadratic) | 0.38 | 3.82 | 0.10 | 0.927517 | −8.61 | 9.36 |
| Transf. (Linear) | 18.70 | 3.67 | 5.09 | 0.014650 | 10.06 | 27.34 |
| Transf.(Quadratic) | 5.70 | 3.82 | 1.49 | 0.232398 | −3.29 | 14.68 |
| IGF-1 (Linear) | 17.03 | 3.67 | 4.64 | 0.018912 | 8.38 | 25.67 |
| IGF-1 (Quadratic) | −4.60 | 3.82 | −1.20 | 0.314842 | −13.58 | 4.39 |
| Alb. × Transf. | 4.85 | 4.80 | 1.01 | 0.386274 | −6.45 | 16.14 |
| Alb. × IGF-1 | −7.68 | 4.80 | −1.60 | 0.207770 | −18.98 | 3.61 |
| Transf. × IGF-1 | −3.99 | 4.80 | −0.83 | 0.467089 | −15.28 | 7.31 |
| Px, max | | | | | | |
| Mean | 0.1830 | 0.0032 | 57.95 | 0.000011 | 0.1756 | 0.1904 |
| Alb. (Linear) | 0.0001 | 0.0017 | 0.08 | 0.943716 | −0.0039 | 0.0042 |
| Alb. (Quadratic) | −0.0084 | 0.0018 | −4.71 | 0.018078 | −0.0126 | −0.0042 |
| Transf. (Linear) | 0.0027 | 0.0017 | 1.57 | 0.215169 | −0.0013 | 0.0067 |
| Transf.(Quadratic) | −0.0014 | 0.0018 | −0.79 | 0.485233 | −0.0056 | 0.0028 |
| IGF-1 (Linear) | 0.0021 | 0.0017 | 1.25 | 0.300568 | −0.0019 | 0.0062 |
| IGF-1 (Quadratic) | −0.0011 | 0.0018 | −0.64 | 0.567571 | −0.0053 | 0.0030 |
| Alb. × Transf. | 0.0028 | 0.0022 | 1.25 | 0.298854 | −0.0025 | 0.0081 |
| Alb. × IGF-1 | −0.0009 | 0.0022 | −0.39 | 0.723255 | −0.0061 | 0.0044 |
| Transf. × IGF-1 | −0.0034 | 0.0022 | −1.51 | 0.227555 | −0.0086 | 0.0019 |

Models presented in Table 10 revealed acceptable value of $R^2$ for Integral (62.7%) but very low value for Px,max (37.9%), indicating that predictable values from the models and experimental measured values were not matching especially for Px,max. In the range analyzed, the quadratic model proposed for Px,max does not represent the system well. The only equation that can be analyzed is the one generated by the Integral (Equation 3).

$$\text{Integral} = 590.8 + 12.9A + 18.7T + 17.0I \quad \text{Eq. 3}$$

For all proteins, the only parameters that are statistically significant are the linear ones. This result matches with the $1^{st}$ RCCD, since this new step aimed to get rid out of the negative interaction between IGF-1 and albumin, accordingly to the new range selected. However, the free term estimated from the model was higher than expected, 590.8. This term represents the overall performance of the model over the range of concentration analyzed for any factor; in biological words, the average cell growth (Integral) was very high despite the concentration of the factors used.

A third step of optimization was performed in order to reduce the cost without losing performance. The same RCCD methodology was used (Table 5) with the following ranges (Table 11):

TABLE 11

Concentration ranges and equivalent costs for each protein in the $3^{nd}$ RCCD

| 3rd RCCD | albumin | U$/L | transferrin | U$/L | IGF-1 | U$/L |
|---|---|---|---|---|---|---|
| +1.68 | 1.2 g/L | 540 | 25 mg/L | 47 | 160 µg/L | 43 |
| +1 | 1.0 g/L | 450 | 22.9 mg/L | 43 | 146 µg/L | 40 |
| 0 | 0.7 g/L | 315 | 20 mg/L | 38 | 125 µg/L | 34 |
| −1 | 0.4 g/L | 180 | 17.1 mg/L | 32 | 104 µg/L | 28 |
| −1.68 | 0.2 g/L | 90 | 15 mg/L | 28 | 90 µg/L | 24 |

In addition to the 14 conditions of RCCD, the "main" central condition was performed in quadruplicates, as usual, in order to estimate the error of the experiment.

The readouts (Integral and Px,max) were calculated for each condition of the third RCCD as shown in Table 12.

TABLE 12

Readouts calculated from the kinetic curves of the third RCCD for recombinant proteins.

| Formulation | Integral ($10^5$ cells h) | Px, Max ($10^5$ cells h$^{-1}$) |
|---|---|---|
| 1 | 325 | 0.1314 |
| 2 | 364 | 0.1481 |
| 3 | 367 | 0.1481 |
| 4 | 352 | 0.1448 |
| 5 | 361 | 0.1335 |
| 6 | 321 | 0.1288 |
| 7 | 332 | 0.1231 |
| 8 | 313 | 0.1210 |

TABLE 12-continued

Readouts calculated from the kinetic curves of the third RCCD for recombinant proteins.

| Formulation | Integral ($10^5$ cells h) | Px, Max ($10^5$ cells h$^{-1}$) |
|---|---|---|
| 9 | 330 | 0.1374 |
| 10 | 311 | 0.1181 |
| 11 | 352 | 0.1341 |
| 12 | 318 | 0.1267 |
| 13 | 335 | 0.1400 |
| 14 | 355 | 0.1338 |
| 15 | 340 | 0.1317 |
| 15 | 325 | 0.1267 |
| 15 | 336 | 0.1276 |
| 15 | 318 | 0.1228 |
| Ctrl+ | 172 | 0.0527 |
| Ctrl+ | 164 | 0.0495 |
| Ctrl+ | 195 | 0.0500 |

Once again, readouts calculated from RCCD were consistently better than the KSR control. Additionally, the variation within the "main" central condition replicates was low, and similarly, KSR replicates had a low deviation as well, indicating reproducible data suitable for building a reliable model. That said, the modeling was performed, and parameters values for a second order model were estimated (Table 13).

TABLE 13

Table of regression from the 3rd RCCD. Coefficient, errors, t, p-value and minimum/maximum limits of each parameter were estimated for every readout (Integral and Px, max). Statistically relevant effects (p < 0.1). $R^2$ = 65.8% for Integral and 86.4% for Px, max.

| Integral | Coefficient | Error | t (3) | p-value | MM (90% conf) | Max (90% conf) |
|---|---|---|---|---|---|---|
| Mean | 329.44 | 4.8 | 67.43 | 0.000007 | 317.96 | 340.92 |
| Alb. (Linear) | 8.42 | 2.64 | 3.18 | 0.49980 | 2.19 | 14.64 |
| Alb. (Quadratic) | −1.49 | 2.75 | −0.54 | 0.625740 | −7.95 | 4.98 |
| Transf. (Linear) | 4.61 | 2.64 | 1.74 | 0.179599 | −1.61 | 10.83 |
| Transf.(Quadratic) | 3.59 | 2.75 | 1.31 | 0.282420 | −2.87 | 10.06 |
| IGF-1 (Linear) | 0.24 | 2.64 | 0.09 | 0.933095 | −5.98 | 6.46 |
| IGF-1 (Quadratic) | 7.12 | 2.75 | 2.59 | 0.081033 | 0.65 | 13.58 |
| Alb. × Transf. | −8.30 | 3.45 | −2.40 | 0.095553 | −16.43 | −0.17 |
| Alb. × IGF-1 | −10.41 | 3.45 | −3.01 | 0.057038 | −18.54 | −2.28 |
| Transf. × IGF-1 | −4.23 | 3.45 | −1.22 | 0.308582 | −12.35 | 3.90 |

| Px, max | Coefficient | Error | t(3) | p-value | Min (90% cof) | Max (90% conf) |
|---|---|---|---|---|---|---|
| Mean | 0.1271 | 0.0018 | 69.59 | 0.000007 | 0.1228 | 0.1314 |
| Alb. (Linear) | 0.072 | 0.0010 | 7.28 | 0.005346 | 0.0049 | 0.0095 |
| Alb. (Quadratic) | 0.0008 | 0.0010 | 0.79 | 0.487887 | −0.0016 | 0.0032 |
| Transf. (Linear) | 0.0013 | 0.0010 | 1.28 | 0.291863 | −0.0011 | 0.0036 |
| Transf.(Quadratic) | 0.0018 | 0.0010 | 1.71 | 0.186200 | −0.0007 | 0.0042 |
| IGF-1 (Linear) | 0.0003 | 0.0010 | 0.29 | 0.788827 | −0.0020 | 0.0026 |
| IGF-1 (Quadratic) | 0.0041 | 0.0010 | 3.95 | 0.028854 | 0.0016 | 0.0065 |
| Alb. × Transf. | −0.0039 | 0.0013 | -3.04 | 0.055694 | −0.0070 | −0.0009 |
| Alb. × IGF-1 | −0.0025 | 0.0013 | −1.95 | 0.145887 | −0.0056 | 0.0005 |
| Transf. × IGF-1 | −0.0022 | 0.0013 | −1.67 | 0.194393 | −0.0052 | 0.0009 |

Similarly to the $2^{nd}$ RCCD, the free term was substantially high when compared to other parameters from the three variables. On the contrary, model estimation had a much better correlation (65.8% for Integral and 86.4% for Px,max), indicating a better fitness. Therefore, the readouts can be represented by the following equations:

$$\text{Integral} = 329.4 + 8.4A + 7.1I^2 - 8.3AT - 10.4AI \quad \text{Eq. 4}$$

$$Px,\max = 10^{-3}(127.1 + 7.2A + 4.1I^2 - 3.9AT) \quad \text{Eq. 5}$$

Consistently, both models readouts share similar information. Linear albumin contribution and its negative interaction with transferrin as well as the quadratic effect from IGF-1 appear in both equations as statistically relevant. The only effect observed on Integral but not on Px,max was the antagonism between albumin and IGF-1; however, this effect was already predicted by the $1^{st}$ RCCD.

Figure 4:
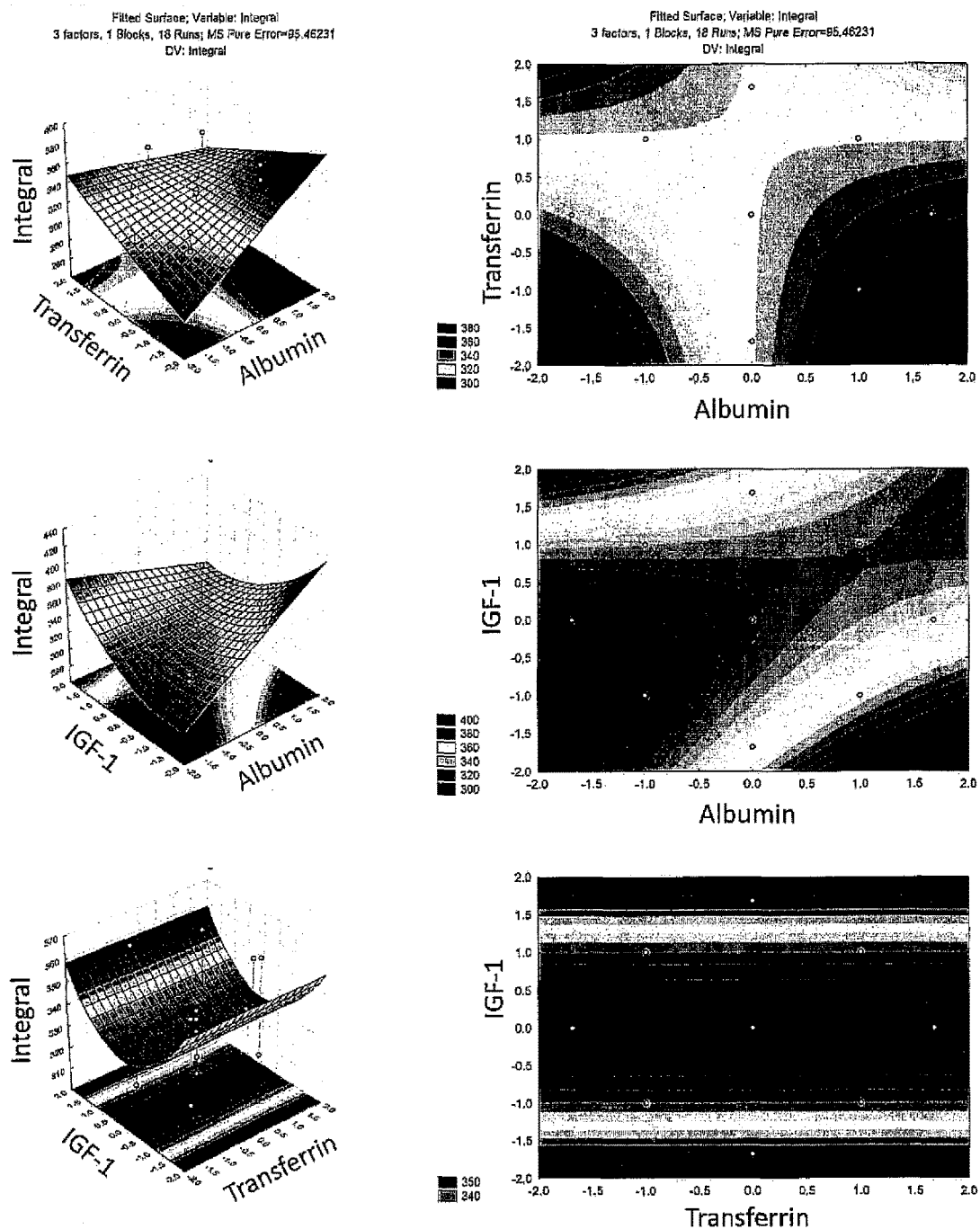
FIG. 4: Surface response and level curves, for integral, made through the model obtained on the 3rd RCCD for recombinant proteins. In each graphic, the missing variable is at the central condition.
Figure 5:
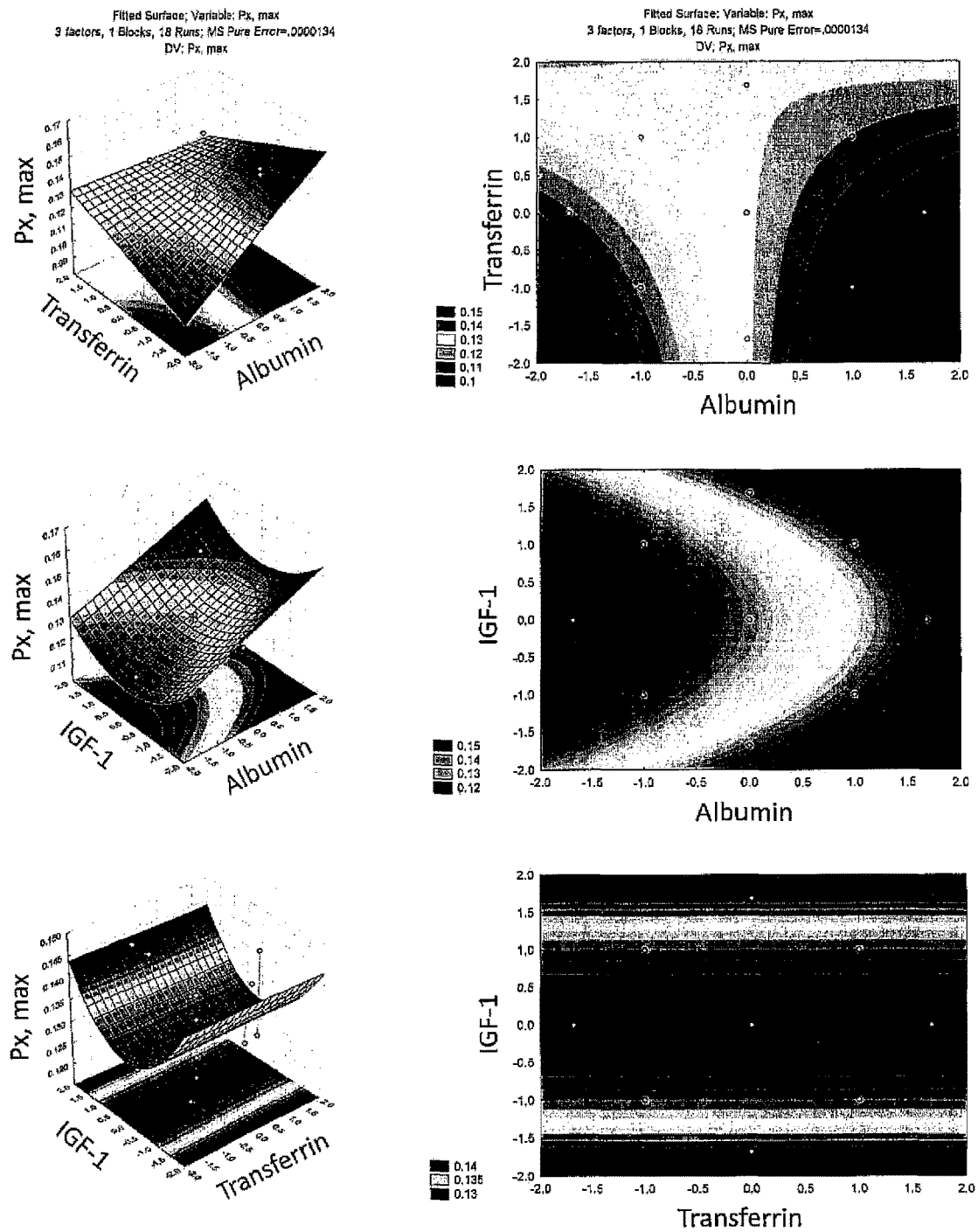
FIG. 5: Surface response and level curves, for Px,max, made through the model obtained on the 3rd RCCD for recombinant proteins. In each graphic, the missing variable is at the central condition.

The surface response and level curves, for each equation, illustrate better how each interaction affects the readouts; in other words, bow each parameter affects cell performance (FIGS. 4 and 5).

The Integral graphics show two regions with a better performance. One with minimum albumin concentration associated with high IGF-I and transferrin concentrations and the other with the exactly opposite condition. This can be easily explained when considering the negative interaction between these proteins.

Similarly, Px,max reveals a similar profile where maximal albumin concentration and minimal concentration of other proteins produced the best readout; however, the converse is not as clear as was seem with the Integral graphics. This difference can be explained since the antagonism effect observed on Integrals parameters is reduced or eliminated on Px,max's parameters.

Considering readouts, having albumin at highest concentration and other proteins at their minimum would be ideal. This would represent a formulation costing around 590 dollars per liter.

However, as predicted by the Integral response, choosing the opposite direction, there are excellent readouts for Integral and Px,max. These new readouts are 7% and 16% lower than the best situation, but they represent a formulation where albumin is in its minimum and transferrin and IGF-1 in its maximum, resulting in 70% reduction of costs (180 dollars per liter). In that sense, aiming for the best cost-effective region, the optimum condition for this step was set at 0.2 g/L of albumin, 25 mg/L of transferrin, and 160 µg/L of IGF-1.

Beyond the three recombinant proteins on the very first screening step (PB12), there were many candidates that could affect the formulation for KSR or FBS replacement.

Since these supplements represent no more than 2% of total cost, irrespective of the amount required, it is desirable to optimize their use so as to have maximal cell performance. This optimization of the less costly supplements should be performed to obtain a better basal media condition before the final optimization of the three more costly components to the media—the three different recombinant protein supplements. A new RCCD was planned for the optimization of citric acid, NEAA and glutamine (Table 14). These factors were chosen based on the fact that they represent the best effect on the P12, after the proteins. The mixture 1:1 of DMEM and Ham's F12 plus: 0.2 g/L of albumin, 25 mg/L of transferrin, 160 µg/L of IGF-1, $0.89 \times 10^{-4}$ mM sodium selenite, BME 110 µM, gentamycin sulfate 50 µg/mL and 8 ng/mL of FGF-2, was used for the formulations. By this time, the concentration of BME was corrected, and a new supplier of DMEM/F12 was used (Millipore, Billerica, Mass.; catalog number DF-041-B instead of Cellgro (Mediatech, Manassas, Va.; catalog number 10-092)).

TABLE 14

3-Var RCCD table, representing 14 different conditions plus the main central condition. The codified values (+1.68, +1, 0, −1 and −1.68) of the matrix are labeled below the design, for each variable.

| DCCR | Citric Acid | NEAA | Glutamine |
|---|---|---|---|
| 1 | +1 | +1 | +1 |
| 2 | +1 | +1 | −1 |
| 3 | +1 | −1 | +1 |
| 4 | +1 | −1 | −1 |
| 5 | −1 | +1 | +1 |
| 6 | −1 | +1 | −1 |
| 7 | −1 | −1 | +1 |
| 8 | −1 | −1 | −1 |
| 9 | +1.68 | 0 | 0 |
| 10 | −1.68 | 0 | 0 |
| 11 | 0 | +1.68 | 0 |
| 12 | 0 | −1.68 | 0 |
| 13 | 0 | 0 | +1.68 |
| 14 | 0 | 0 | −1.68 |
| 15 | 0 | 0 | 0 |
| +1.68 | 20.1 mg/L | 3.25% (v/v) | +3.0 mM |
| +1 | 17.2 mg/L | 2.85% (v/v) | +2.4 mM |
| 0 | 12.9 mg/L | 2.25% (v/v) | +1.5 mM |
| −1 | 8.6 mg/L | 1.65% (v/v) | +0.6 mM |
| −1.68 | 5.6 mg/L | 1.25% (v/v) | +0.0 mM |

Figure 6:
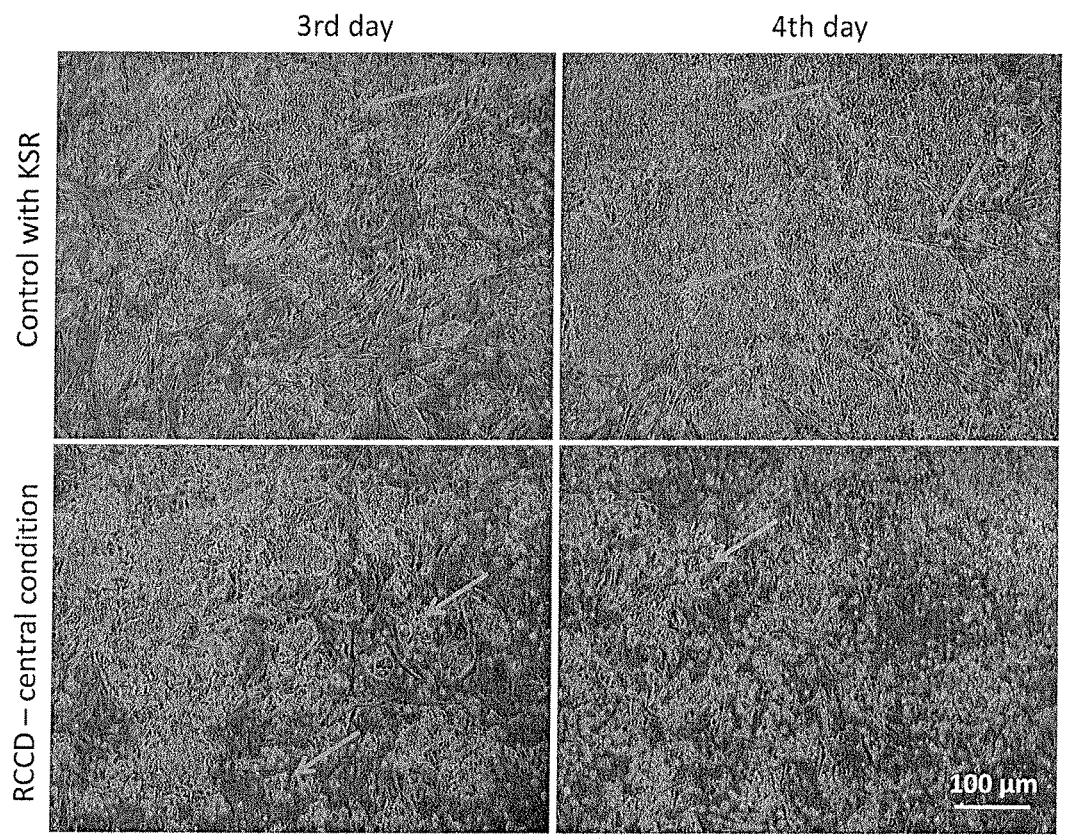
FIG. 6: H-9s cultured at media with KSR and one the central formulation from RCCD. Arrows indicate good colonies formation/development, orange arrow point to differentiation/cell death and red arrow suggest cell death in suspension.

Surprisingly, during the cell counting of H-9s cells, it was observed that all conditions related to the RCCD had an intense cell death; however, the ones used with the KSR media kept growing and still forming colonies, although noticeably slowly (FIG. 6).

Interestingly, it was observed that media pH was more acid, turning yellow fast even with reduced amount of cells on KSR media. Since pH changes are mainly related to the buffers in the media, a comparison between Millipore media and Cellgro was performed. The amount of sodium bicarbonate in Cellgro was twice more (2.4 g/L) than Millipore (1.2 g/L); however, HEPES buffer was the same amount (15 mM) for both suppliers. Surprisingly, all commercial available media (mTeSR1, Stempro) for ES have in its composition 1.2 g/L of bicarbonate. Additionally, most recommended basal media used together with KSR has 1.2 g/L as well.

A simple test was performed with KSR formulation, just changing basal media supplier and consequently just changing the amount of buffer. All samples with extra amount of bicarbonate were able to perform better, growing as predicted. Millipore's basal media with extra buffer was able to perform as well as Cellgro media, proving that bicarbonate was the main reason for decreased cell growth with KSR.

After buffer correction, the RCCD was performed again (Table 14), however an intense cell death was observed one more time under all conditions except for the KSR control. While buffer concentration seemed to be really important, something else was happening causing a more drastic response in the RCCD conditions.

Figure 7:
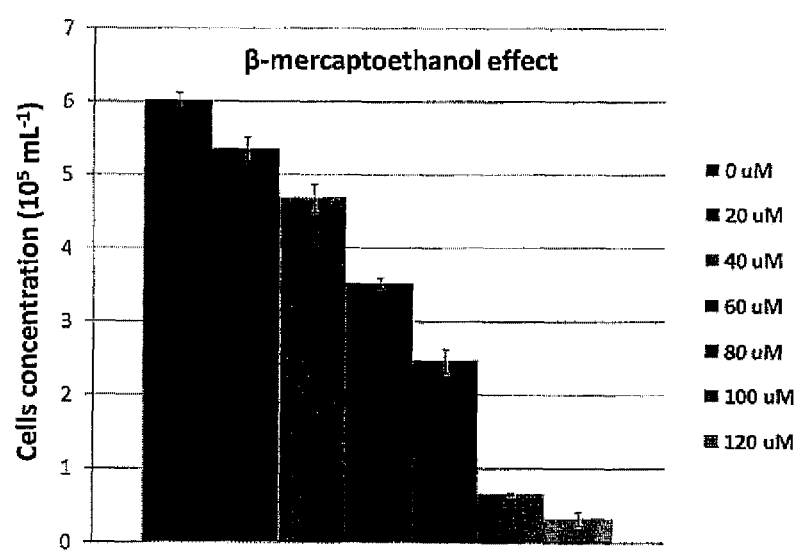
FIG. 7: H-9s concentration after 3 days of culture in low protein based formulation with different BME concentrations. Error bars were generated through independent quadruplicates.

Having a meticulous comparison between all RCCDs performed, it was noticed that BME concentration was different due to supplier differences. However, BME concentration itself would not explain why the cells did not grow properly on RCCD, but grew well on KSR media, since the BME concentration was present in the KSR control formulation as well. Still, considering that BME is not just an antioxidant but a denaturizing chemical as well, it is expected that this compound would have a greater effect on media formulated with low amount of proteins. With the new RCCD, reducing the amount of albumin was aimed, due to its cost. Since albumin is the most abundant protein in the media, the total amount of proteins is being greatly reduced in every RCCD making the BME denaturizing effect more pronounced in our formulations than KSR's. To prove this point, different concentration of BME were used in a low protein medium (the "main" central condition from the last RCCD) and cell growth seems to be linearly dependent on BME (FIG. 7) with increasing BME concentration promoting less cell growth.

It is clear that even in very small concentration (20 µM) BME have a statistically negative effect on ES cell growth for low protein amount formulation ($p<0.01$, t-test). Astonishingly, BME is normally added and recommended in KSR based media and feeder free media like mTeSR1 and StemPro. However, the negative effect of this compound is probably buffered by the huge amount of proteins that these media got, around 10 grams per liter, while the invention provides at least 20 times less. This discovery represents a breakthrough in terms of what are the real needs of an ES cell, drastically changing the media and cell's environment.

Taking these last discoveries into consideration, the RCCD from NEAA, citric acid and glutamine (Table 14) was repeated but this time without BME and with increased concentration of sodium bicarbonate. As expected, all conditions performed way better and readouts were able to be calculated from the kinetics curves from H-9s (Table 15).

TABLE 15

Readouts calculated from the kinetic curves of the first RCCD for NEAA, citric acid and glutamine.

| Formulation | Integral ($10^5$ cells h) | Px, Max ($10^5$ cells $h^{-1}$) |
|---|---|---|
| 1 | 441 | 0.0824 |
| 2 | 468 | 0.1124 |
| 3 | 586 | 0.1303 |
| 4 | 497 | 0.1106 |
| 5 | 470 | 0.1068 |
| 6 | 440 | 0.0927 |
| 7 | 546 | 0.1277 |
| 8 | 533 | 0.1209 |
| 9 | 499 | 0.1035 |
| 10 | 487 | 0.1121 |
| 11 | 415 | 0.0859 |
| 12 | 533 | 0.1202 |
| 13 | 537 | 0.1161 |
| 14 | 582 | 0.1303 |
| 15 | 585 | 0.1393 |
| 15 | 589 | 0.1421 |
| 15 | 596 | 0.1340 |

TABLE 15-continued

Readouts calculated from the kinetic curves of the first RCCD for NEAA, citric acid and glutamine.

| Formulation | Integral ($10^5$ cells h) | Px, Max ($10^5$ cells $h^{-1}$) |
|---|---|---|
| 15 | 568 | 0.1353 |
| Ctrl+ | 339 | 0.0557 |
| Ctrl+ | 344 | 0.0605 |
| Ctrl+ | 356 | 0.0560 |

As shown by the readouts, all conditions performed better than the ones with KSR (positive control). However, at this time, there is a distinct difference within the results from RCCD conditions suggesting that some components may be in excess or just in an inhibitory concentration in a certain range. For instance, putting Tables 14 and 15 side-by-side, it is easy to notice that in all conditions where NEAA is at high concentrations (+1 and +1.68), the readouts are decreased; however, at minimum concentrations (−1.68), the readouts are not as good as well. This observation suggests regions (between −1 and +1) where NEAA should give the best performance for ES cell growth. Trying to find these regions, a model was created (Table 16).

TABLE 16

Table of regression from the 1st RCCD for NEAA, citric acid and glutamine.
Coefficient, errors, t, p-value and minimum/maximum limits of each parameter were estimated for every readout (Integral and Px, max). Statistically relevant effects ($p < 0.1$).
$R^2$ = 90.7% for Integral and 89.5% for Px, max.

|  | Coefficient | Error | t (3) | p-value | Min (90% conf) | Max (90% conf) |
|---|---|---|---|---|---|---|
| Integral |  |  |  |  |  |  |
| Mean | 584/93 | 5.88 | 99.51 | 0.000002 | 571.10 | 598.77 |
| Citric Ac. (Linear) | 1.63 | 3.19 | 0.51 | 0.645114 | −5.87 | 9.12 |
| Citric Ac. (Quadratic) | −33.83 | 3.31 | −10.22 | 0.001998 | −41.62 | −26.04 |
| NEAA (Linear) | −39.65 | 3.19 | −12.45 | 0.001118 | −47.15 | −32.16 |
| NEAA(Quadratic) | −40.48 | 3.31 | −12.23 | 0.001177 | −48.28 | −32.69 |
| Glutamine (Linear) | 2.10 | 3.19 | 0.66 | 0.556653 | −5.40 | 9.60 |
| Glutamine (Quadratic) | −10.20 | 3.31 | −3.08 | 0.054125 | −17.99 | −2.41 |
| Citric Ac. × Transf. | −0.88 | 4.16 | −0.21 | 0.846551 | −10.67 | 8.92 |
| Citric Ac. × IGF-1 | 2.50 | 4.16 | 0.60 | 0.590559 | −7.30 | 12.30 |
| NEAA × IGF-1 | −12.27 | 4.16 | −2.95 | 0.060120 | −22.07 | −2.48 |
| Px, max |  |  |  |  |  |  |
| Mean | 0.1377 | 0.0019 | 74.36 | 0.000005 | 0.1333 | 0.1420 |
| Citric Ac. (Linear) | −0.0020 | 0.0010 | −1.97 | 0.143184 | −0.0043 | 0.0004 |
| Citric Ac. (Quadratic) | −0.0104 | 0.0010 | −9.98 | 0.002140 | −0.0129 | −0.0080 |
| NEAA (Linear) | −0.0112 | 0.0010 | −11.16 | 0.001541 | −0.0136 | −0.0088 |
| NEAA(Quadratic) | −0.0121 | 0.0010 | −11.61 | 0.001374 | −0.0146 | −0.0096 |
| Glutamine (Linear) | −0.0010 | 0.0010 | −0.96 | 0.407876 | −0.0033 | 0.0014 |
| Glutamine (Quadratic) | −0.0050 | 0.0010 | −4.77 | 0.017533 | −0.0074 | −0.0025 |
| Citric Ac. × Transf. | 0.0004 | 0.0013 | 0.29 | 0.791782 | −0.0027 | 0.0035 |
| Citric Ac. × IGF-1 | −0.0039 | 0.0013 | −2.98 | 0.058565 | −0.0070 | −0.0008 |
| NEAA × IGF-1 | −0.0053 | 0.0013 | −4.04 | 0.027317 | −0.0084 | −0.0022 |

Figure 8:
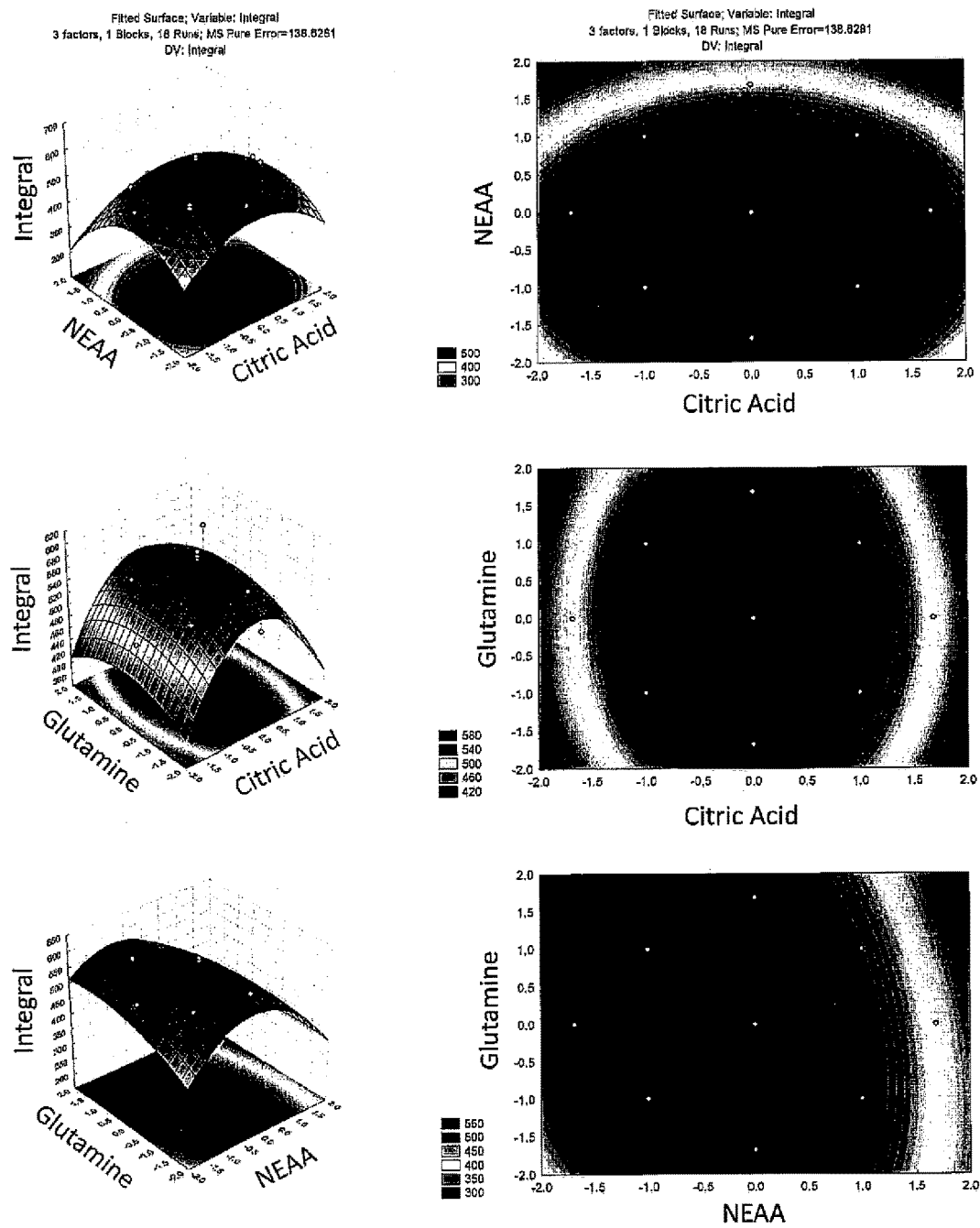
FIG. 8: Surface response and level curves, for integral, made through the model obtained on the 1st RCCD for NEAA, citric acid and glutamine. In each graphic, the missing variable is at the central condition.
Figure 9:
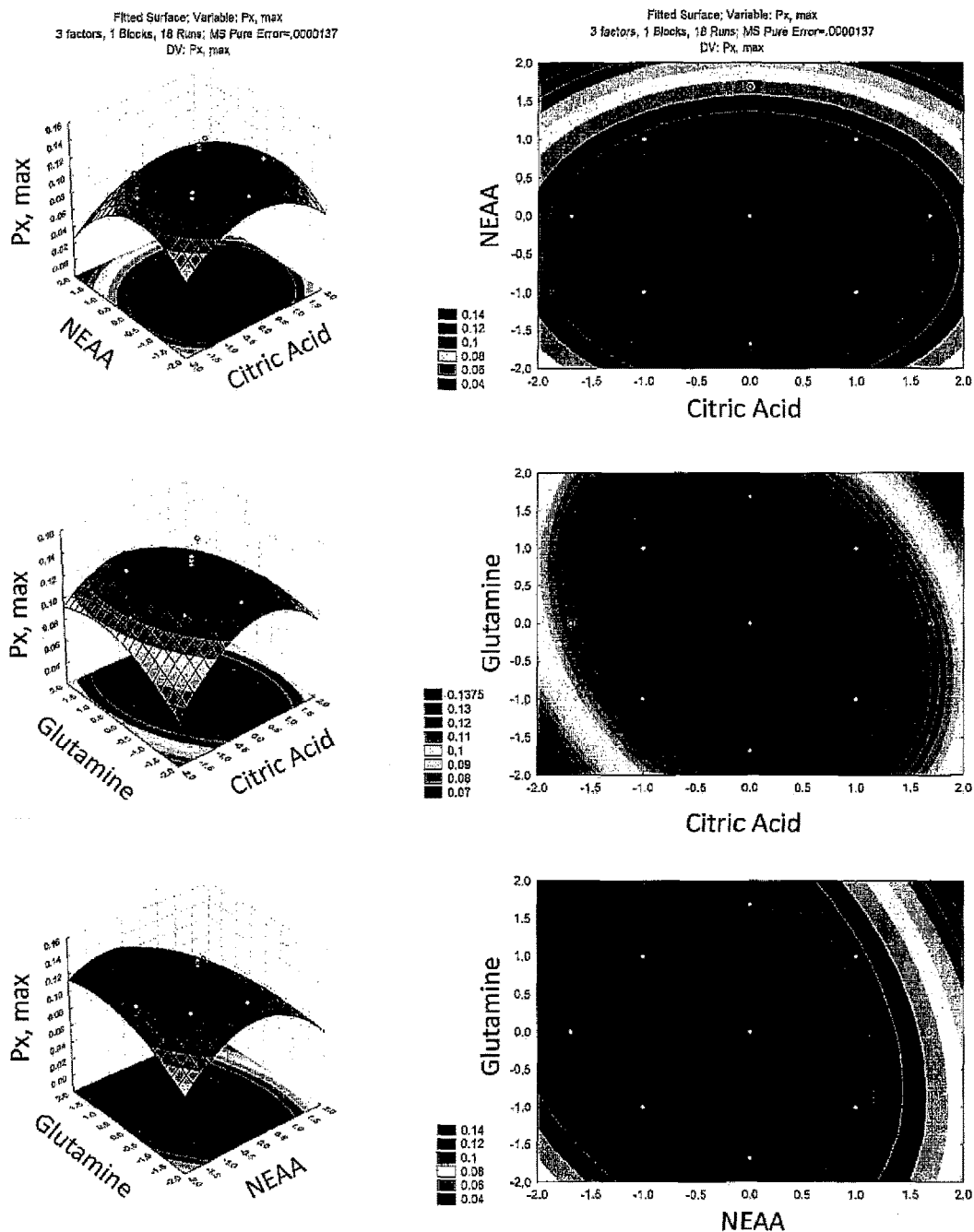
FIG. 9: Surface response and level curves, for Px,max, made through the model obtained on the 1st RCCD for NEAA, citric acid and glutamine. In each graphic, the missing variable is at the central condition.

Through the analysis of Table 16, it is noticeable that most of the supplements showed negative quadratic effect or interaction. From a mathematical point of view, this means that the curvature of the curve is facing down, thus, having a point of maximum. Additionally, the correlation factors were high for both readouts (90.7% for integral and 89.5% for Px,max), so they can be expressed according to the following equations (equations 6 and 7) and the following surfaces (FIGS. 8 and 9):

$$\text{Integral}=584.9-33.8Ac^2-39.6N-40.5N^2-10.2G^2-12.3NG \quad \text{Eq. 6}$$

$$Px,\text{max}=10^{-3}(137.7-10.4Ac^2-11.2N-12.1N2-5.0G2-3.9AcG-5.3NG) \quad \text{Eq. 7}$$

(Ac is the value of the citric acid, N is the value of non-essential amino acids and G is the value of glutamine—in codified values from −1.68 to +1.68).

Through the analysis of the curves, it is clear that there are regions of maxima. As mentioned before, the impact of these 3 supplements on the cost is low; hence, the concentrations chosen for an optimized medium will aim to get the best cell performance or readout. Since the point of maximum in an equation is the one where the derivative is equal to zero, for each model (integral and Px,max), the derivative was calculated giving the following equations for integral:

$$-67.6Ac=0 \quad \text{Eq. 8}$$

$$-39.6-81N-12.3G=0 \quad \text{Eq. 9}$$

$$-20.4G-12.3N=0 \quad \text{Eq. 10}$$

From equation 8, the optimum of citric acid is shown on the codified value of 0, or central condition. Replacing equation 9 into equation 10, glutamine and NEAA were calculated resulting in 0.32 and -0.54, respectively.

In the same fashion, the calculation was performed for Px,max:

$$-20.8Ac-3.9G=0 \quad \text{Eq. 11}$$

$$-11.2-24.2N-5.3G=0 \quad \text{Eq. 12}$$

$$-10.0G-3.9Ac-5.3N=0 \quad \text{Eq. 13}$$

Replacing equation 11 into equation 13, the ratio between glutamine and NEAA was obtained. Through this ratio and further replace into equation 12, values of 0.30 and -0.59 were obtained for glutamine and NEAA. Replacing these values at equation 11, the codified value for citric acid is close to zero.

By comparing optimum values calculated from integral and Px,max it is easy to recognize that they are very close to each other for each supplement. This scenario indicates that different readouts are pointing to the same direction showing consistency. After de-codifying values, the supplement concentration was adopted as: 12.9 mg/L of citric acid, 1.95% of NEAA and 2 mM of glutamine.

Considering making further improvements related to serum replacement, a 2-var RCCD was performed to check the influence of 2 categories of trace elements. They are known as group B and group C elements, and their composition are related to salts made of heavy metals (Si, Ni, Cr, Co, Cd, etc.). Interestingly, none of the groups of elements, B or C, were able to have any impact on cell growth, meaning that models generated by the RCCD resulted in parameter with no statistical relevance. Surprisingly, it is well-known that most used media have these group elements in their composition (LUDWIG et al., 2006a; WANG et al., 2007), one more indication that these media were not optimized and somehow formulated empirically.

Besides the optimization steps done so far, it was checked if the property of the media was related specifically to a certain brand of the components. One of the most expensive components, the CellPrime rAlbumin AF-S (Millipore, Billerica, Mass.; catalog number 9501), was replaced for a new recombinant protein called CellPrime rAlbumin AF-G (Millipore, Billerica, Mass.; catalog number 9301), being almost 25 times cheaper. The main difference between them is how they are produced, while AF-S is produced in *Saccharomyces cerevisiae* the AF-G is produced in *Aspergillus oryzae*. However, same standards as "free of animal compounds" and "endotoxin levels" were still taken in consideration in order to insure quality. In the same fashion, new recombinant Long R3 IGF-1 (Sigma-Aldrich, St. Louis, Mo.; catalog number 85580C) was used.

That said, a new optimization of recombinant proteins was performed as the 3-variable RCCD matrix (Table 5), but this time the concentration range of most abundant proteins, albumin and transferrin, were decreased since there was no more BME in the media (Table 17).

TABLE 17

Concentration ranges and equivalent costs for each protein in the $4^{th}$ RCCD

| 4° RCCD | albumin | U$/L | transferrin | U$/L | IGF-1 | U$/L |
|---|---|---|---|---|---|---|
| +1.68 | 0.60 g/L | 18 | 18.0 mg/L | 34 | 240 µg/L | 15 |
| +1 | 0.49 g/L | 15 | 15.6 mg/L | 29 | 216 µg/L | 13 |

TABLE 17-continued

Concentration ranges and equivalent costs for each protein in the $4^{th}$ RCCD

| 4° RCCD | albumin | U$/L | transferrin | U$/L | IGF-1 | U$/L |
|---|---|---|---|---|---|---|
| 0 | 0.32 g/L | 10 | 12.0 mg/L | 23 | 180 µg/L | 11 |
| −1 | 0.15 g/L | 5 | 8.40 mg/L | 16 | 144 µg/L | 9 |
| −1.68 | 0.04 g/L | 1 | 6.00 mg/L | 11 | 120 µg/L | 7 |

The mixture 1:1 of DMEM and Ham's F12, with non-reduced sodium bicarbonate (2.4 g/L) plus: 2 mM glutamine, 12.9 mg/L citric acid, 1.95% NEAA, 0.89×10$^{-4}$ mM sodium selenite and 8 ng/mL of FGF-2, was used for the formulations. The kinetics curves form H-9s were obtained for 14 conditions from RCCD, plus quadruplicates of the main central condition and duplicates of positive control with KSR. The readouts were once again calculated (Table 18) as specified before.

TABLE 18

Readouts calculated from the kinetic curves of the fourth RCCD for recombinant proteins.

| Formulation | Integral (10$^5$ cells h) | Px, Max (10$^5$ cells h$^-$) |
|---|---|---|
| 1 | 437 | 0.1985 |
| 2 | 447 | 0.1840 |
| 3 | 460 | 0.1709 |
| 4 | 442 | 0.1817 |
| 5 | 419 | 0.1722 |
| 6 | 428 | 0.1798 |
| 7 | 444 | 0.1936 |
| 8 | 417 | 0.1683 |
| 9 | 436 | 0.1798 |
| 10 | 413 | 0.1745 |
| 11 | 423 | 0.1755 |
| 12 | 394 | 0.1703 |
| 13 | 483 | 0.2004 |
| 14 | 474 | 0.1903 |
| 15 | 458 | 0.1772 |
| 15 | 457 | 0.1850 |
| 15 | 432 | 0.1824 |
| 15 | 452 | 0.1837 |
| ctrl+ | 163 | 0.0558 |
| ctrl+ | 166 | 0.0522 |

Just looking at the readouts, it is difficult to check the real contribution of each factor for this specific range. For a more detailed analysis, a model was built as before (Table 19).

TABLE 19

Table of regression from the 4th RCCD. Coefficient, errors, t, p-value and minimum/maximum limits of each parameter were estimated for every readout (Integral and Px, max). Statistically relevant effects (p < 0.1). $R^2$ = 88.0% for Integral and 69.0% for Px, max.

| Integral | Coefficient | Error | t (3) | p-value | Min (90% conf) | Max (90% conf) |
|---|---|---|---|---|---|---|
| Mean | 449.52 | 6.11 | 73.52 | 0.000006 | 435.13 | 463.91 |
| Alb. (Linear) | 8.51 | 3.31 | 2.57 | 0.082734 | 0.71 | 16.31 |
| Alb. (Quadratic) | −8.80 | 3.44 | −2.56 | 0.083444 | −16.91 | −0.70 |
| Transf. (Linear) | 1.17 | 3.31 | 0.35 | 0.746663 | −6.63 | 8.97 |
| Transf.(Quadratic) | −14.34 | 3.44 | −4.17 | 0.025183 | −22.45 | −6.24 |
| IGF-1 (Linear) | 3.10 | 3.31 | 0.94 | 0.418003 | −4.69 | 10.90 |
| IGF-1 (Quadratic) | 10.30 | 3.44 | 2.99 | 0.058070 | 2.20 | 18.40 |
| Alb. × Transf. | −0.48 | 4.33 | −0.11 | 0.918732 | −10.67 | 9.71 |
| Alb. × IGF-1 | −1.15 | 4.33 | −0.27 | 0.807863 | −11.34 | 9.04 |
| Transf. × IGF-1 | −7.98 | 4.33 | −1.84 | −.162420 | −18.17 | 2.21 |

TABLE 19-continued

Table of regression from the 4th RCCD. Coefficient, errors, t, p-value and minimum/maximum limits of each parameter were estimated for every readout (Integral and Px, max). Statistically relevant effects (p < 0.1). $R^2$ = 88.0% for Integral and 69.0% for Px, max.

| Px, max | Coefficient | Error | t (3) | p-value | Min (90% cof) | Max (90% conf) |
|---|---|---|---|---|---|---|
| Mean | 0.1821 | 0.0017 | 105.75 | 0.000002 | 0.1781 | 0.1862 |
| Alb. (Linear) | 0.0022 | 0.0009 | 2.36 | 0.099028 | 0.0000 | 0.0044 |
| Alb. (Quadratic) | −0.0019 | 0.0010 | −1.94 | 0.147899 | −0.0042 | 0.0004 |
| Transf. (Linear) | 0.0021 | 0.0009 | 2.26 | 0.108801 | −0.0001 | 0.0043 |
| Transf.(Quadratic) | −0.0034 | 0.0010 | −3.49 | 0.039692 | −0.0057 | −0.0011 |
| IGF-1 (Linear) | 0.0028 | 0.0009 | 3.01 | 0.057074 | 0.0006 | 0.0050 |
| IGF-1 (Quadratic) | 0.0046 | 0.0010 | 4.70 | 0.018271 | 0.0023 | 0.0068 |
| Alb. × Transf. | 0.0050 | 0.0012 | 4.07 | 0.026821 | 0.0021 | 0.0078 |
| Alb. × IGF-1 | −0.0018 | 0.0012 | −1.45 | 0.244169 | −0.0046 | 0.0011 |
| Transf. × IGF-1 | −0.0009 | 0.0012 | −0.77 | 0.495846 | −0.0038 | 0.0019 |

Figure 10:
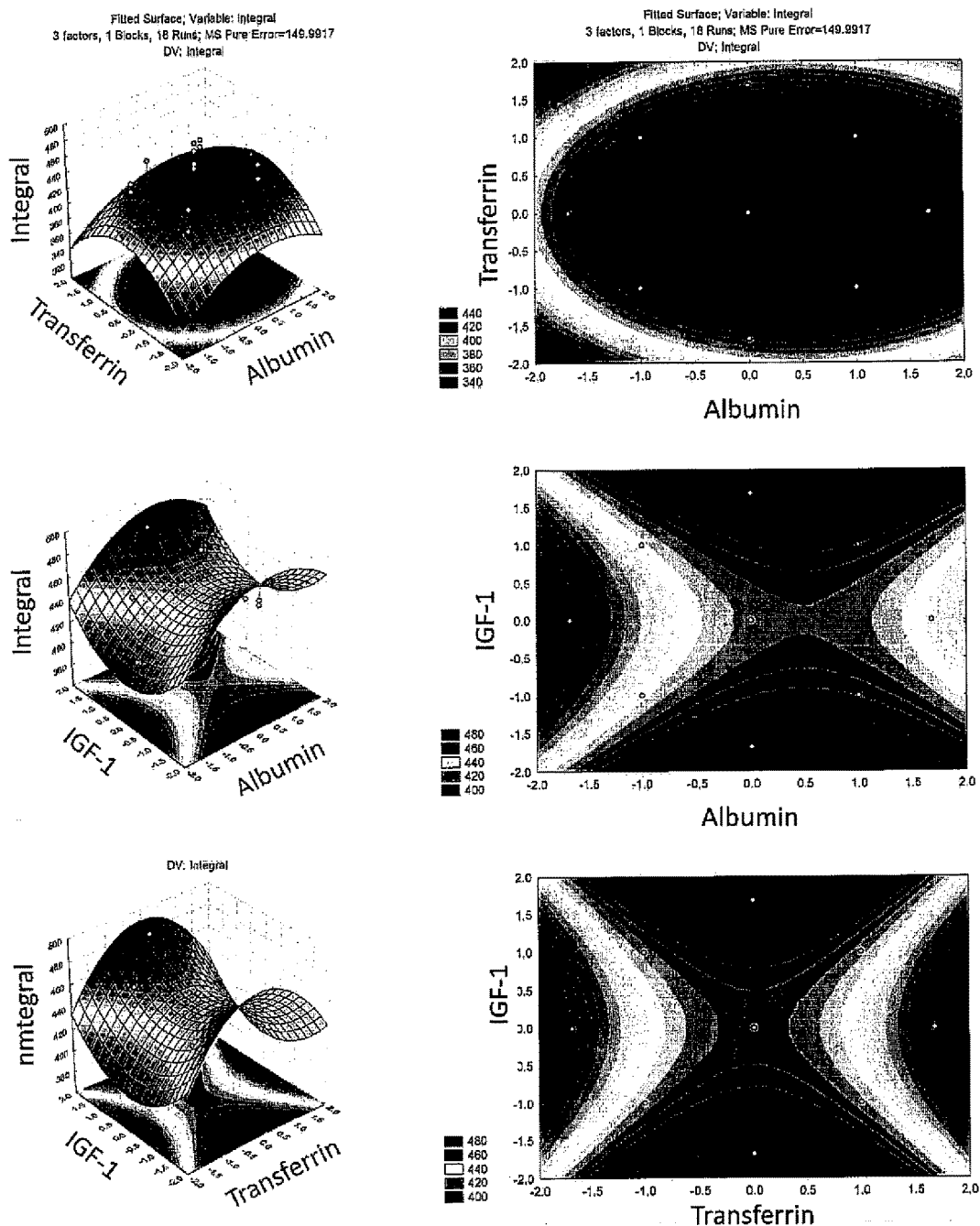
FIG. 10: Surface response and level curves, for integral, made through the model obtained on the $4^{th}$ RCCD for recombinant proteins. In each graphic, the missing variable is at the central condition.
Figure 11:
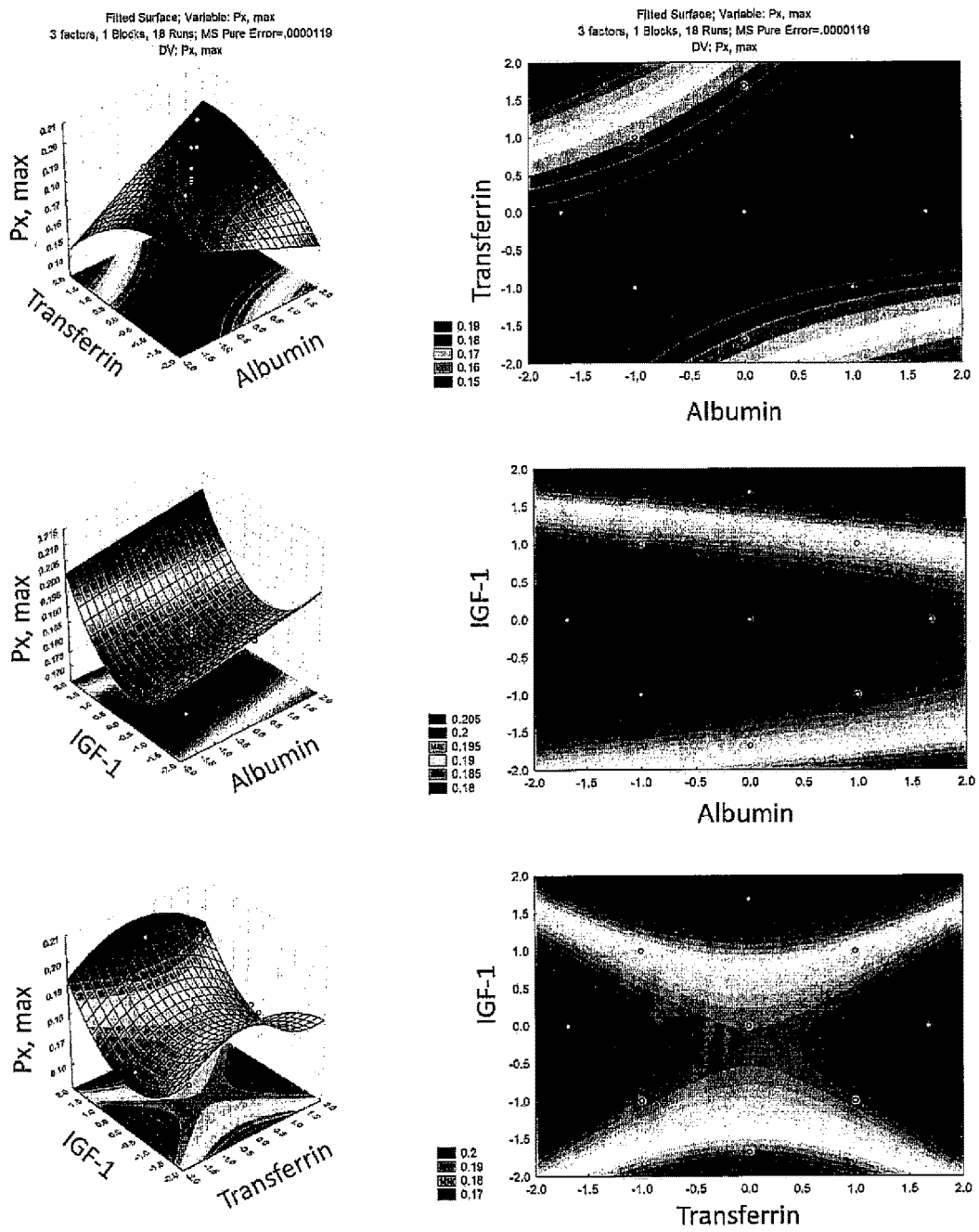
FIG. 11: Surface response and level curves, for Px,max, made through the model obtained on the $4^{th}$ RCCD for recombinant proteins. In each graphic, the missing variable is at the central condition.

The generated model has a good fit for both readouts ($R^2$=88% for integral and 69% for Px,max) with parameters that had a small but significantly contribution for each factor. The presence of negative quadratic effects once again suggests ranges of optimum that can be seen from the plotting of the following equations (FIG. 10 and FIG. 11).

$$\text{Integral}=449.5+8.5A-8.8A^2-14.3T^2+10.3I^2 \qquad \text{Eq. 14}$$

$$\text{Prod,max}=10^{-3}(182.1+2.2A-3.4T+2.8I+4.6I^2+5AT) \qquad \text{Eq. 15}$$

Through the observation of curves and equations, it is easy to conclude that the best concentration to work with transferrin is the central condition. In order to calculate the optimum albumin concentration, the derivative from equation 14 was done resulting in:

$$8.5-17.6A=0 \qquad \text{Eq. 16}$$

From equation 16, the codified value of 0.48 or 0.4 g/L of albumin represents the best condition.

For IGF-1, integral readout showed dubious effect and for that reason, Px,max readout was used to support which condition would fit best in an optimized media. The Px,max surface showed optimum regions where albumin and transferrin are increased due to its positive interaction; however, this interaction is just clearly observed when the model is too extrapolated (codified values>2), generating uncertainty. However, when looking at the best condition calculated from integral (0 for transferrin and 0.48 for albumin) on Px,max graphics, there are already outstanding predicted results. For this reason, the concentrations of albumin and transferrin were set according to the integral readout. When taking into consideration IGF-1, Px,max readout showed a better performance on high concentrations than lower concentrations due to the positive linear contribution, and for this reason the +1.68 value was chosen.

Surprisingly, when taking a closer look into the model and the graphics, there are predictable conditions where the albumin concentration is zero (codified value−1.93). Very interestingly, equations give acceptable readouts when albumin is completely depleted, representing around 15% worse performance than the optimum condition. That said, once again, it is evident that BME had a major effect on media formulation and its removal made the culture of ES able in conditions in the absence of albumin.

Still, since the optimized condition already shows a considerable decrease of costs when comparing to the very early steps or even the main competitor (KSR), it was desirable to keep it instead of trying to get one condition that could be cheaper with worse results like the one without albumin.

That said, the final formulation obtained from all steps of optimization aiming to replace KSR based media was: mixture 1:1 of DMEM and Ham's F12, with non-reduced sodium bicarbonate (2.4 g/L) plus 2 mM glutamine (total of 4.5 mM), 129 mg/L citric acid, 1.95% NEAA, 0.89×10$^{-4}$ mM sodium selenite, 0.4 g/L of recombinant albumin, 12 mg/L of recombinant transferrin, 240 µg/L of recombinant IGF-1 and 8 ng/mL of FGF-2.

In order to check the efficiency and the robustness of this new media, named MaSeR (Marinho Serum Replacement), the two most used cell lines, H-9 and HUES9, were cultured in parallel with KSR based media (Wicell) and MaSeR, for several passages (>5).

Figure 12:
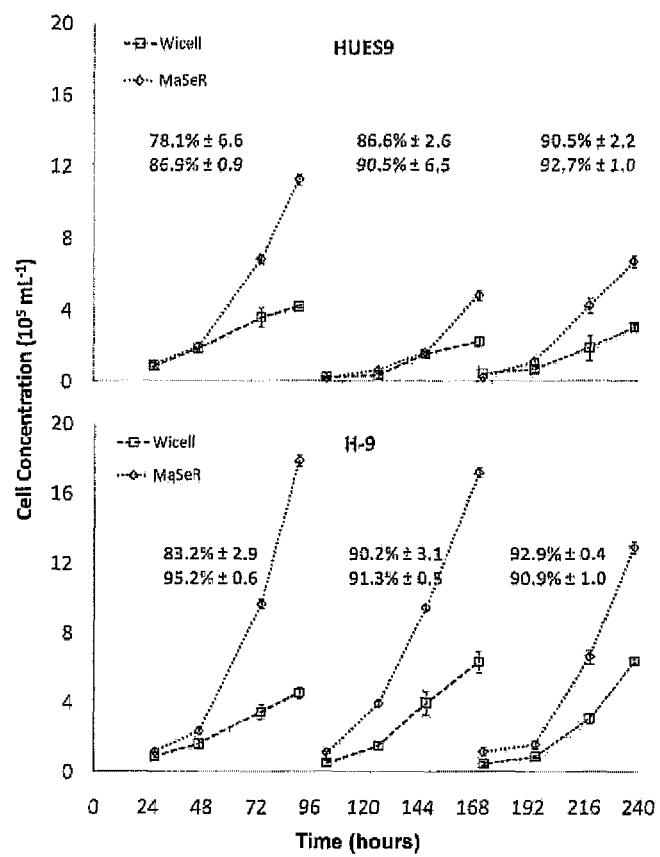
FIG. 12: HUES9 and H-9 kinetics growth over 3 passages in Wicell and MaSeR. On the top of each curve is shown the value of viability on the last day of culture. Error bars were obtained from independent triplicates.

Both lines were enzymatically dissociated, cells well suspended before plating ~1-2×10$^{-4}$ cells/cm$^2$) in tissue culture plates containing inactivated MEFs, either with KSR- or MaSeR-based media. Their kinetic growth and cell viability were monitored for 3 passages (240 hours), and in every passage, cells were plated at the same concentration for a good comparison (FIG. 12).

From the analysis of the kinetics growth, it is noticeable that the developed media has a better performance, in terms of cell growth, than the KSR based media. And that profile is maintained through the passages. Additionally, the media shows its versatility with an improved performance for HUES9 cells as well, proving that although developed with H-9 cells, it maintains its advantage with other ES cell lines as well. Furthermore, viability in almost all time points showed to be satisfactory (>90%).

Likewise, when calculating the same readouts as from RCCD steps, the values from KSR-based media and MaSeR-based media are statistically different (p<0.1, t-test). While for MaSeR, H-9 had 422.+−.0.89 and HUES9 had 201.+−.0.98 values for integral, KSR resulted in just 173.+−.0.23 and 107.+−.0.51 respectively. Similarly, Px,max performed, 0.23.+−.0.037 versus 0.079.+−.0.019 (for H-9) and 0.110.+−.0.047 versus 0.040.+−.0.011 (for HUES9).

Besides growth analysis, the cell recover after thawing process was evaluated. Enzymatically frozen H-9s were thaw in parallel in MaSeR- and KSR-based media at same density. Cells plated with MaSeR recovered faster having to be passaged twice before even KSR media finished its recovery. This translates to about 120 times faster recover rate.

Figure 13:
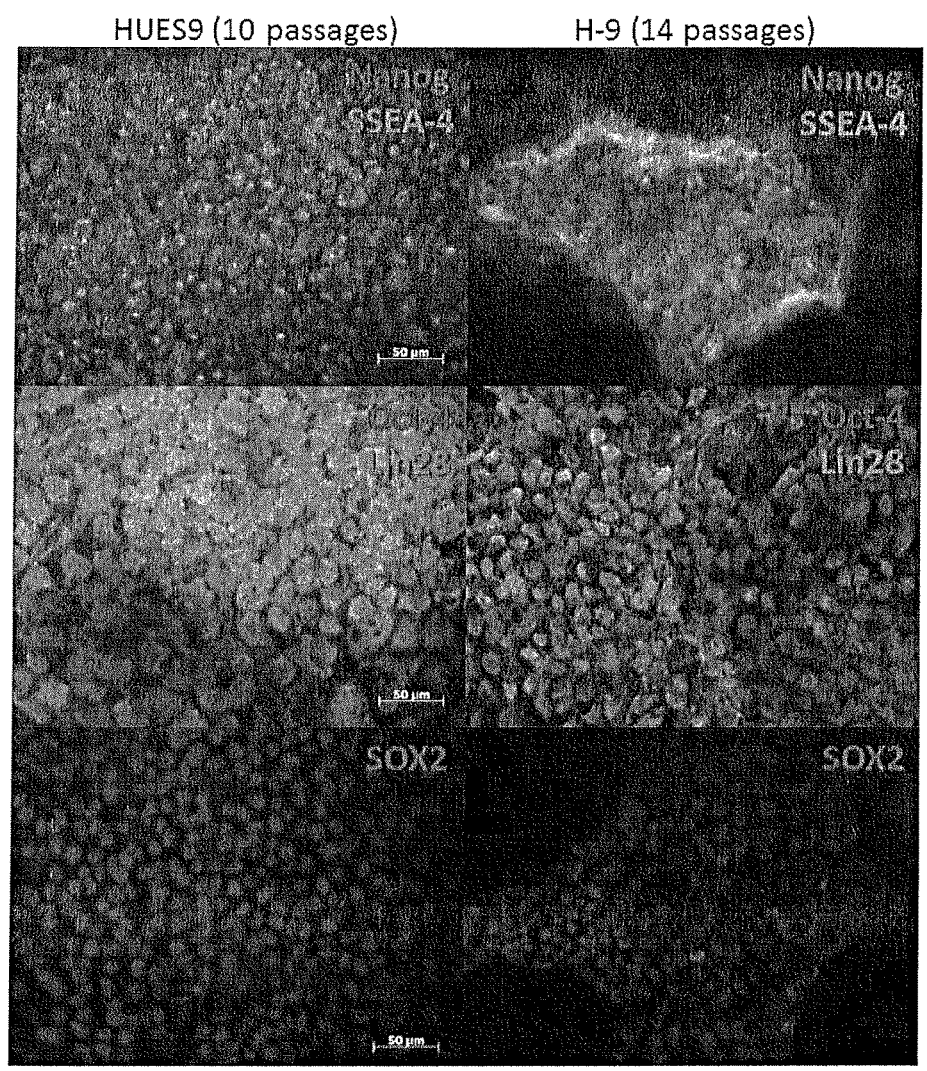
FIG. 13: Immunofluorescence staining for H-9 and HUES9 cells in MaSeR media for 14 and 10 passages, respectively. Markers: Nanog, Oct-4, SOX2, SSEA-4 and Lin28.

Pluripotency was assayed for both cells lines after several passages (>10). Most classic pluripotency markers (Oct-4, Lin28, Nanog, SSEA-4, SOX2) were found on ES colonies cultured in MaSeR by immunofluorescence staining (FIG. 13).

Immuno-stainings panels showed all pluripotency markers to maintain their patterns. Oct-4, Nanog and SOX2 had sharp nuclear stains, while Lin28 had a strong cytoplasmic profile with halos around the nucleus and SSEA-4 kept its diffuse appearance. This qualitative analysis confirmed that MaSeR kept the pluripotency of cells. Additionally, through FACs analysis, Nanog and SSEA-4 had similar levels of expression when compared to KSR-based media (6 passages), showing equivalency on quantitative data.

Besides cell growth and pluripotency, karyotype was performed since aneuploidy related to chromosomes 12, 17 and 21 are somehow connected to growth advantage in vitro (SEOL, 2008). H-9s cultured on MaSeR were sent to Cell Line Genetics for G band. The report from the company affirms that the cells are euploid, having no alterations in its karyotype. That said, the improved performance related to cell growth is not related to any selection in terms of aneuploidy of cells but just for the fact that MaSeR is an optimized media that promoted normal growth of ES cells.

Figure 14:
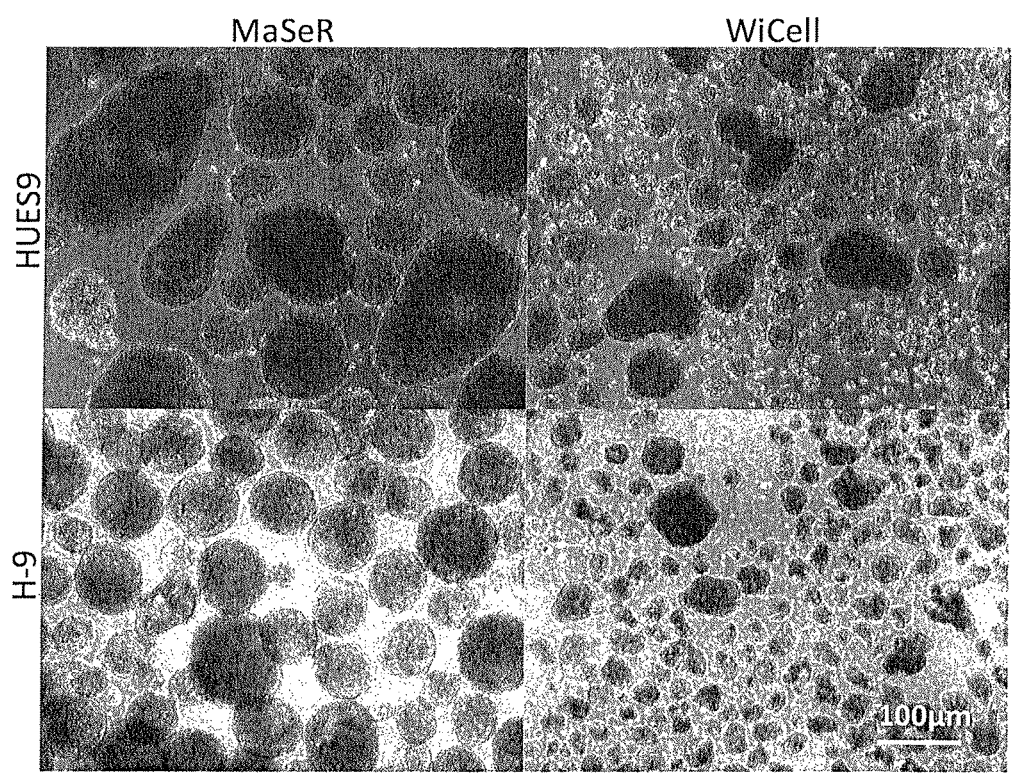
FIG. 14: EBs photos from H-9 and HUES9 after being cultured with MaSeR and KSR based media without FGF-2 for 3 days.
Figure 15:
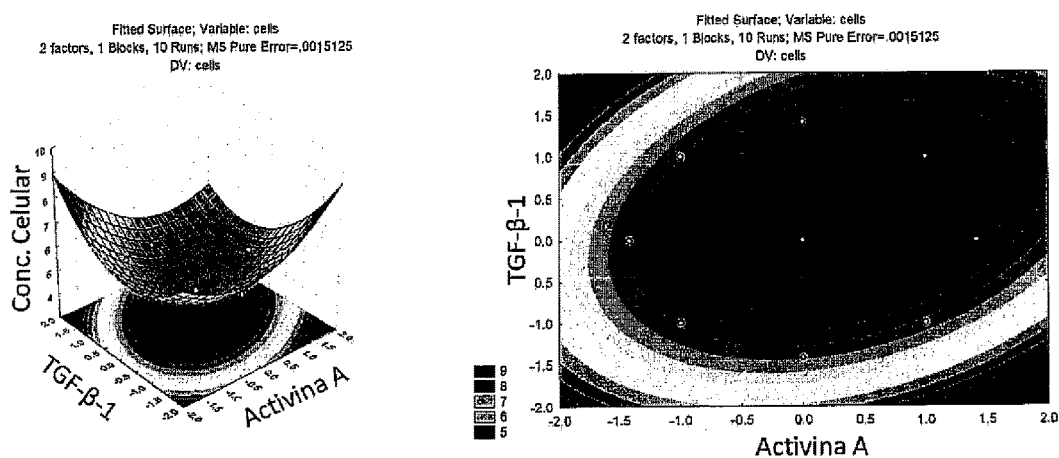
FIG. 15: Surface response and level curve, for self-renew, made through the model obtained on the RCCD for feeder free condition.

In terms of differentiation, H-9 and HUES9 culture on MaSeR and KSR-based media were passaged as clumps to non-adherent plates on the top of a shaker (80 RPM) in order to form embryonic bodies (EBs). To differentiate the cells, FGF-2 was removed from both media. Surprisingly, the faster growth was observed with the differentiated cells as well, and the EBs cultured in MaSeR without FGF-2 were formed faster than the ones cultured in KSR based media without FGF-2, as shown on FIG. 14.

It is clear that EBs formed while in MaSeR without bFGF developed faster and better when considering the defined borders and cavitation formation.

Moreover besides EB formation, cells were injected in nude mice for teratoma evaluation. Both cell lines cultured with MaSeR were able to develop teratomas containing cells from the 3 different germ layers.

Besides all the current features, since MaSeR was developed without the presence of any animal compounds it is expected that cells cultured with it do not incorporate Neu5Gc, a non-human sugar known to be incorporated on human cells and evoke immune responses. H-9s cultured on the top of microcarriers and being fed daily with MaSeR conditioned from MEFs showed a dramatic drop in terms of Neu5Gc incorporation, when compared to cells cultured under the same condition but with KSR-based media, from 77.9±3.2% to 2.7±0.7%. Interestingly, this is the first time that a media showed a decreasing of non-human sugar incorporation.

Hence, MaSeR is cheaper than current ES available feeder media, representing just 70% of the final price from KSR-based media.

Now that KSR and FBS have been removed from ES culture, the next step aiming a defined environment free of animal compounds is the removal of feeders from the system. A new media (MaSeR2) was formulated in order to remove MEFs.

In a first moment, MaSeR2 was created by adding extra factors to MaSeR resulting in mixture 1:1 of DMEM and Ham's F12, with non-reduced sodium bicarbonate (2.4 g/L) (DMEM/F12; Mediatech, Manassas, Va.; catalog number 10-092) plus 2 mM L-glutamine (total of 4.5 mM; Invitrogen, Carlsbad, Calif.; catalog number 25030-149), 12.9 mg/L citric acid (Sigma-Aldrich, St. Louis, Mo.; catalog number C2404), 1.95% NEAA (Mediatech, Manassas, Va.; catalog number 25-025-C1), $0.89 \times 10^{-4}$ mM sodium selenite (Sigma-Aldrich, St. Louis, Mo.; catalog number S5261), 0.4 g/L of recombinant albumin (Millipore, Billerica, Mass.; catalog number 9301), 12 mg/L of recombinant transferrin (InVitria, Fort Collins, Colo.; catalog number 777TRF029), 240 μg/L of recombinant IGF-1 (Sigma-Aldrich, St. Louis, Mo.; catalog number 85580C), $9.79 \times 10^{-1}$ mM of γ-aminobutyric acid (GABA; Sigma-Aldrich, St. Louis, Mo.; catalog number A5835), $9.84 \times 10^{-4}$ mM pipecolic acid (PA; Sigma-Aldrich, St. Louis, Mo.; catalog number P2519), 0.5% chemically defined lipids concentrated (CDL; Invitrogen, Carlsbad, Calif.; 11905031) and 60 ng/mL of FGF-2 (Peprotech, Rocky Hill, N.J.; catalog number 100-18B).

In general, supplements were added to the stirred media in the following order: acids first, then salts, followed by albumin, then transferring and IGF-1, and lastly, FGF-2 and TGF-beta-1.

Interestingly, in that non-optimized condition, both H-9s, HUES9 and iPS were already able to form colonies and keep their pluripotency, even with FGF-2 concentrations lower than previously claimed at feeder free concentrations (LEVENSTEIN, 2006; LUDWIG, 2006). Aiming to improve the efficacy of the media, stimulating other pathways, besides the FGF-path, were explored. The Nodal/Activin pathway is related to pluripotency/self-renew (XIAO, 2006), than the factors from TGF superfamily. Activin A (Peprotech, Rocky Hill, N.J.; catalog number 120-14E) and TGF-beta-1 (Peprotech, Rocky Hill, N.J.; catalog number 100-21C), were investigated in a 2-variable RCCD (Table 20).

TGF-beta-1 was resuspended in a citric acid and activin A in PBS.

TABLE 20

Concentration ranges for each protein, Activin A and TGF-beta-1 in the first RCCD for feeder free condition.

| RCCD feeder-free | Activin A | TGF-β-1 |
| --- | --- | --- |
| +1.41 | 10 ng/mL | 2 ng/mL |
| +1 | 8.5 ng/mL | 1.7 ng/mL |
| 0 | 5 ng/mL | 1 ng/mL |
| −1 | 1.5 ng/mL | 0.3 ng/mL |
| −1.41 | 0 ng/mL | 0 ng/mL |

In these experiments, a wild-type iPS line was used. In the same fashion as the feeder conditions, cells were homogenously inoculated in several plates in each different formulation. The main difference in this step was the readout analyzed. Kinetic growth were not obtained due to the problems related to managing several feeder-free plates. Thus, instead of calculating integral and Px,max, two other readouts were used. The first one was the final cell growth achieved, called here as self-renew and the other one was percent of pluripotency, obtained from FACs analyzes by the dual staining with SSEA-4 and Nanog.

Interestingly when doing the model for pluripotency with Statistica software, there were no parameters either related to Activin A or TGF-beta-1 that were statistically relevant (p>0.1). However, when looking into self-renew all factors had a very clear contribution (Table 21).

TABLE 21

Table of regression from the first feeder-free RCCD. Coefficient, errors, t, p-value and minimum/maximum limits of each parameter were estimated for self-renew. Statistically relevant effects ($p < 0.1$). $R^2 = 90.3\%$.

| Self-renew | Coefficient | Error | t(3) | p-value | Min (90% conf) | Max (90% conf) |
|---|---|---|---|---|---|---|
| Mean | 4.413 | 0.027 | 160.4545 | 0.003968 | 4.239 | 4.586 |
| Activin A (Linear) | −0.430 | 0.027 | −15.6356 | 0.040661 | −0.604 | −0.256 |
| Activin A (Quadratic) | 0.798 | 0.036 | 21.9391 | 0.028997 | 0.568 | 1.028 |
| TGF-β-1 (Linear) | −0.508 | 0.027 | −18.4906 | 0.034396 | −0.682 | −0.335 |
| TGF-β-1 (Quadratic) | 0.936 | 0.036 | 25.7188 | 0.024741 | 0.706 | 1.165 |
| Activin A × TGF-β-1 | −0.550 | 0.039 | −14.1421 | 0.044941 | −0.796 | −0.304 |

Analyzing the model, it is clear that TGF-beta-1 and Activin A have similar parameters. Additionally, they got a negative interaction with each other; meaning that, from an optimization point of view, if one is raised the other should be diminished. Taking a look into the surface gives a better clue of the best regions.

Taking the surface into account, there are three better choices, where two of them are represented by one factor at maximum and other at minimum and the other choice is the two supplements at minimum. Although, the last option may sound better when considering cost reduction, thinking about future steps of optimizations may be the worst choice. This is because the minimum concentration represents absence of the factor, in that sense, it not feasible to extrapolate the graphs for codified values below −1.41. Thus, since both factors have very similar contributions, in terms of cell performance, it will not matter what factor will be kept in highest concentration and the other in lowest. Therefore, TGF-beta-1 was chosen as the factor that would be kept in the highest concentration, since in the range analyzed, it represents five times less cost.

Figure 16:
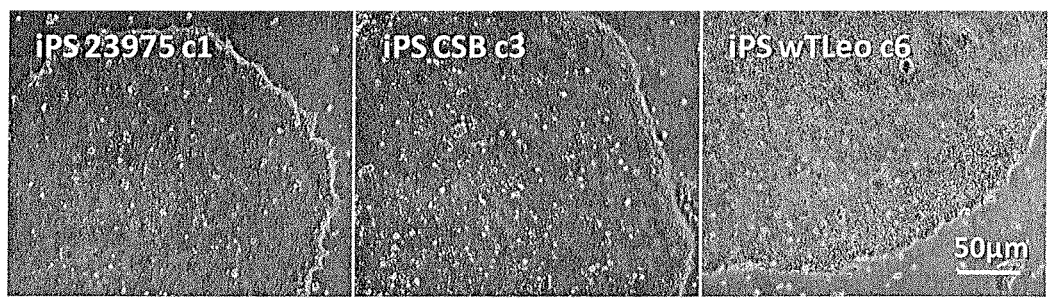
FIG. 16: Bright field photos from 3 different iPS lines being cultured on MaSeR2 over 5 passages.

Remarkably, after this single step, several pluripotent cells consisting of two ES lines and six iPS lines kept their standard morphology (FIG. 16) after 5 passages being cultured in MaSeR2—mixture 1:1 of DMEM and Ham's F12, with non-reduced sodium bicarbonate (2.4 g/L) plus 2 mM glutamine, 12.9 mg/L citric acid, 1.95% NEAA, 0.89× $10^{-4}$ mM sodium selenite, 0.4 g/L of rhAlb, 12 mg/L of rhTransf, 240 μg/L of rhIGF-1, 9.79×$10^{-1}$ mM GABA, 9.84×$10^{-4}$ mM PA, 0.5% CDL, 60 ng/mL of FGF-2 and 2 ng/mL of TGF-beta-1.

Additionally, independent assays with PACs, showed high percentages (>85%) of dual staining for SSEA-4 and Nanog, evidencing that cells are still pluripotent.

As in the same fashion as in the feeder condition, no aneuploidy was reported according to Cell Line Genetics company and teratomas were formed after injection in nude mice.

Also, MaSeR2 was able to clean cells previously contaminated with Neu5Gc, reducing its levels from 56.6+5.1% to 10.8+1.2% within just six passages.

Still, since MaSeR2 is a low content media, it represents around 50% off of cost when compared to other media, despite being a completely defined media formulated with recombinant proteins.

REFERENCES

CHIN, A. C. P.; FONG, W. J.; GOH, L.-T.; et al.; 2007, "Identification of proteins from feeder conditioned medium that support human embryonic stem cells". Journal of Biotechnology, v. 130 (3), pp. 320-328.

FERNANDES, A. M.; MELETTI, T.; GUIMAR E S, R.; et al.; 2010, "Worldwide survey of published procedures to culture human embryonic stem cells". Cell Transplantation, doi: 10.3727/096368909X485067.

GARCIA-GONZALO, F. R.; BELMONTE, J. C. L; 2008, "Albumin-Associated Lipids Regulate Human Embryonic Stem Cell Self-Renewal". Plos One, v1., pp. 1-10.

LEVENSTEIN, M. E.; LUDWIG, T. E.; XU R.; et al.; 2006. "Basic Fibroblast Growth Factor Support of Human Embryonic Stem Cell Self-Renewal". Stein Cells, v. 24, pp. 568-574.

LIM, J. W.; BODNAR, A.; 2002, "Proteome analysis of conditioned medium from mouse embryonic fibroblast feeders layers which support the growth of human embryonic stein cells". Proteomics, v. 2, pp. 1187-1203.

LUDWIG, T. E.; LEVENSTEIN, M. E.; JONES, J. M.; et al.; 2006a, "Derivation of human embryonic stem cells in defined conditions". Nature Biotechnology, pp. 1-3

RODRIGUES, M. I.; IEMMA, A. F.; 2005, "Estrategia Experimental para Fatoriais Fracionados e Delineamento Composto Central Rotacional (DCCR)". In: RODRIGUES, M. I.; IEMMA, A. F.; Planejamento de Experimentos e Otimizacao de Processos—Uma estrategia Sequencial de Planejamentos, Capitulo 5, Caso do Pao.

POUTON, C. W.; HAYNES, J. M.; 2007, "Embryonic stem cells as a source of models for drug discovery". Nature Reviews, v. 6, pp. 605-616.

PROWSE, A. B. J.; MCQUADE, L. R.; BRYANT, K. J.; et al.; 2005, "A proteome analysis of conditioned media from human neonatal fibroblasts used in the maintenance of human embryonic stem cells". Proteomics, v. 5.

THOMSON, J. A.; ITSKOVITZ-ELDOR, J.; SHAPIRO, S. S.; et al.; 1998, "Embryonic stein cell lines derived from human blastocysts". Science, v. 282 (5391), pp. 1145-1147.

WANG, L.; Li, L.; MENENDEZ, P.; et al.; 2005a, "Human embryonic stem cells maintained in the absence of mouse embryonic fibroblasts or conditioned media are capable of hematopoietic development". Blood, v. 105, pp. 4598-4603.

What is claimed is:

1. A method of maintaining and expanding stem cells in an undifferentiated state in culture comprising culturing the stem cells in a defined low protein culture medium, wherein the amount of protein in said defined low protein medium is about 20× less than in a standard media, which standard media contains 10 g/liter protein, and which low protein culture medium is feeder-free, xeno-free, free of any denaturing agents, and free of animal-derived or human-derived proteins, so as to maintain and expand the stem cells in the undifferentiated state in culture, wherein the medium comprises sodium selenite, an organic acid from the tricarboxylic acid cycle and a combination of growth factors selected from the group consisting of FGF-2 recombinant protein, an IGF-1 recombinant protein or recombinant insulin, a Transferrin recombinant protein, and a TGF beta 1 recombinant protein.

2. The method of claim 1, wherein the organic acid in the medium is selected from a group consisting of citric acid, cis-aconitic acid, isocitiric acid, alpha-ketoglutaric acid, succinic acid, fumaric acid, malic acid, and oxalic acid, or mixtures thereof.

3. The method of claim 1, wherein the defined culture medium further comprises one or more of chemically or recombinantly produced albumin, vitamin B, glutamine and Chemically Defined Lipid concentrate (CDL).

4. The method of claim 1, wherein the defined culture medium further comprises chemically or recombinantly produced:
(a) Pipecolic acid or a derivative or equivalent thereof,
(b) γ-aminobutyric acid (GABA) or a derivative or equivalent thereof,
(c) Albumin, and
(d) A combination of HEPES and sodium bicarbonate.

5. The method of claim 1, wherein the defined culture medium further comprises chemically or recombinantly produced:
(a) citric acid,
(b) Nonessential amino acids;
(c) glutamine,
(d) Chemically Defined Lipid concentrate (CDL),
(e) FGF-2,
(f) IGF-1 or insulin,
(g) Transferrin,
(h) TGF beta 1,
(i) Pipecolic acid,
(j) γ-aminobutyric acid (GABA),
(k) Albumin, and
(l) A combination of HEPES and sodium bicarbonate.

6. The method of claim 1, wherein the defined culture medium further comprises chemically or recombinantly produced:
(a) citric acid is present in an amount in the range of 11.61-14.19 mg/L,
(b) Nonessential amino acids is in an amount in the range of 1.75-2.15% (v/v);
(c) Glutamine is present in an amount in the range of 4.05-4.95 mM,
(d) Chemically Defined Lipid concentrate (CDL) is present in an amount in the range of 0.45-0.55% (v/v),
(e) FGF-2 is present in an amount in the range of 54-66 ng/mL,
(f) IGF-1 is present in an amount in the range of 216-264 ug/L,
(g) Transferrin is present in an amount in the range of 10.8-13.2 mg/L,
(h) TGF beta 1 is present in an amount in the range of 1.8-2.2 ng/mL,
(i) Pipecolic acid is present in an amount in the range of $8.86\text{-}10.82 \times 10^{-4}$ mM,
(j) γ-aminobutyric acid (GABA) is present in an amount in the range of $8.81\text{-}10.77 \times 10^{-1}$ mM,
(k) Albumin is present in an amount in the range of 0.36-0.44 g/L, and
(l) A combination of the amount of the sodium bicarbonate is in the range of 1.2 g/L-2.8 g/L, and the amount of HEPES is in the range of 10 mM-18 mM.

7. The method of claim 1, wherein the stem cells so cultured are grown in and fed by the defined culture medium which is replaced after about every 24-72 hours.

8. The method of claim 7, wherein the cells are passaged between 0 hours and 72 hours after reaching passing confluence.

9. The method of claim 1, wherein the stem cells are cultured on a chemically or recombinantly produced matrix.

* * * * *